United States Patent
Ho et al.

(10) Patent No.: US 6,462,063 B1
(45) Date of Patent: Oct. 8, 2002

(54) C-PROTEINASE INHIBITORS

(75) Inventors: Wen-Bin Ho, Los Altos, CA (US); Udo Bauer, Lauf (DE)

(73) Assignee: Fibrogen, Inc., South San Francisco, CA (US)

(*) Notice: Subject to any disclaimer, the term of this patent is extended or adjusted under 35 U.S.C. 154(b) by 0 days.

(21) Appl. No.: 09/497,946

(22) Filed: Feb. 4, 2000

(51) Int. Cl.[7] .................. C07D 233/70; A61K 31/4166
(52) U.S. Cl. .................. 514/389; 514/391; 514/341; 546/274.4; 548/319.5
(58) Field of Search ................. 548/319.5; 514/391, 514/389

(56) References Cited

FOREIGN PATENT DOCUMENTS

| EP | 0 640 594 A1 | 3/1995 |
|---|---|---|
| WO | WO 95/33709 | 12/1995 |
| WO | WO 97/05865 | 2/1997 |
| WO | WO 98/34918 | 8/1998 |

OTHER PUBLICATIONS

CA 112:235019, Barraclough et al. 1990.*
Bode et al., "The X–Ray Crystal Structure of the Catalytic Domain of Human Neutrophil Collagenase Inhibited by a Substrate Analogue Reveals the Essentials for Catalysis and Specificity," EMBO J. 13(6):1263–1269 (1994).
Davidson et al., "Procollagen Processing: Limited Proteolysis of COOH–Terminal Extension Peptides by a Cathepsin–Like Protease Secreted by Tendon Fibroblasts," Eur. J. Biochem. 100:551 (1979).
Duksin et al., "The Role of Glycosylation in the Enzymatic Conversion of Procollagen Collagen: Studies using Tunicamycin and Concanavalin A," Arch. Biochem. Biophys. 185(2):326–332 (1978).
Fertala et al., "Self–Assembly into Fibrils of Collagen II by Enzymic Cleavage of Recombinant Procollagen II," J. Biol. Chem. 269(15):11584 (1994).
Goldberg et al., "Procollagen Peptidase: Its Mode of Action on the Native Substrate," Cell 4:45–50 (1975).
Grams et al., "Structure Determination and Analysis of Human Neutrophil Collagenase Complexed with a Hydroxamate Inhibitor," Biochem. 34:14012–14020 (1995).
Hojima et al., "Type I Procollagen Carboxyl–Terminal Proteinase From Chick Embryo Tendons," J. Biol. Chem. 260(29):15996–16003 (1985).
Kessler et al., "Partial Purification and Characterization of a Procollagen C–Proteinase from the Culture Medium of Mouse Fibroblasts," Collagen Relat. 6:249–266 (1986).
Kessler et al., "Bone Morphogenetic Protein–1: The Type I Procollagen C–Proteinase," Science 271:360–362 (1996).
Kessler and Adar, "Type I Procollagen C–Proteinase From Mouse Fibroblasts: Purification and Demonstration of a 55–kDa Enhancer Glycoprotein," Eur. J. Biochem. 186:115–121 (1989).
Kessler and Goldberg, "A Method for Assaying the Activity of the Endopeptidase Which Excises the Nonhelical Carboxyterminal Extensions from Type I Procollagen", Anal. Biochem. 86:463–469 (1978).
Krumme et al., "Hydroxamate Derivates of Substrate–Analogous Peptides Containing Aminomalonic Acid are Potent Inhibitors of Matrix Metalloproteinases," FEBS Lett. 436:209–212 (1998).
Lee et al., "Transforming Growth Factor–βRegulation of Bone Morphogenetic Protein–1/Procollagen C–Proteinase and Related Proteins in Fibrogenic Cells and Keratinocytes," J. Biol. Chem. 272(30):19059–19066 (1997).
Leung et al., "Separate Amino and Carboxyl Procollagen Peptidases in Chick Embryo Tendon," J. Biol. Chem. 254(1):224–232 (1979).
Li et al., "The C–Proteinase that Processes Procollagens to Fibrillar Collagens is Identical to the Protein Previously Identified as Bone Morphogenic Protein–1," Proc. Natl. Acad. Sci. USA 93:5127–5130 (1996).
Njieha et al., "Partial Purification of a Procollagen C–Proteinase. Inhibition by Synthetic Peptides and Sequential Cleavage of Type I Procollagen," Biochemistry 23:757–764 (1982).
Prockop et al., "Procollagen N–Proteinase and Procollagen C–Proteinase. Two Unusual Metalloptroteinases that are Essential for Procollagen Processing Probably Have Important Roles in Development and Cell Signaling," Matrix Biology 16:399–408 (1998).
Ryhänen et al., "Conversion of Type II Procollagen to Collagen In Vitro: Removal of the Caroxy–Terminal Extension in Inhibited by Several Naturally Occurring Amino Acids, Polyamines, and Structurally Related Compounds," Arch. Biochem. Biophys. 215(1):230–236 (1982).
Suzuki et al., "Failure of Ventral Body Wall Closure in Mouse Embryos Lacking a Procollagen C–Proteinase Encoded by Bmp 1, a Mammalian Gene Related to *Drosophila Tolloid*," Development 122:3587–3595 (1996).
Takahara et al., "Type I Procollagen COOH–Terminal Proteinase Enhancer Protein: Identification, Primary Structure, and Chromosomal Localization of the Cognate Human Gene (PCOLCE)," J. Biol. Chem. 269(42):26280–26285 (1994).

* cited by examiner

*Primary Examiner*—Jane Fan
(74) *Attorney, Agent, or Firm*—FibroGen, Inc.

(57) ABSTRACT

The present invention relates to a novel class of N,N'-di substituted hydantoin hydroxamates capable of inhibiting C-proteinase, and to their use to regulate, modulate and/or inhibit abnormal collagen formation as a therapeutic approach towards the treatment of fibrotic disorders.

28 Claims, No Drawings

C-PROTEINASE INHIBITORS

1. FIELD OF THE INVENTION

The present invention relates to a novel class of organic molecules capable of inhibiting the enzyme C-proteinase, pharmaceutical compositions comprising the C-proteinase inhibitory compounds and methods of using the compounds and compositions to regulate, modulate and/or inhibit collagen production and/or maturation as a therapeutic approach towards the treatment or prevention of myriad diseases related to, or associated with, unregulated collagen production.

2. BACKGROUND OF THE INVENTION

Collagen Structure

At present, nineteen different types of collagens have been identified. These collagens, which include fibrillar collagen types I, II and III, are synthesized as procollagen precursor molecules which contain peptide extensions at both their amino- and carboxy-termini. These peptide extensions, referred to as "pro-regions," are designated as N- and C-propeptides, respectively.

The pro-regions are typically cleaved upon secretion of the procollagen triple helical precursor molecule from the cell to yield a mature triple helical collagen molecule. Upon cleavage, the "mature" collagen molecule is capable of association, for example, into highly structured collagen fibers. See e.g., Fessler and Fessler, 1978, *Annu. Rev. Biochem.* 47:129–162; Bornstein and Traub, 1979, in: The Proteins (eds. Neurath, H. and Hill, R. H.), Academic Press, New York, pp. 412–632; Kivirikko et al., 1984, in: *Extracellular Matrix Biochemistry* (eds. Piez, K. A. and Reddi, A. H.), Elsevier Science Publishing Co., Inc., New York, pp. 83–118; Prockop and Kivirikko, 1984, *N. Engl. J. Med.* 311:376–383; Kuhn, 1987, in: *Structure and Function of Collagen Types* (eds. Mayne, R. and Burgeson, R. E.), Academic Press, Inc., Orlando, Fla., pp. 1–42.

Diseases Associated With The Abnormal Production of Collagen

A variety of critical diseases have been linked to inappropriate or unregulated collagen production and/or maturation. These diseases include pathological fibrosis or scarring (including endocardial sclerosis), idiopathic interstitial fibrosis, interstitial pulmonary fibrosis, perimuscular fibrosis, Symmers' fibrosis, pericentral fibrosis, hepatitis, dermatofibroma, binary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture and payronles disease. Further fibrotic disorders may be induced or initiated by surgery, including scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. One strategy for the treatment of these diseases is to inhibit the pathological overproduction of collagen. Thus, identification and isolation of molecules which control, inhibit and/or modulate the production of collagen are of major medical interest.

Relationship Between Collagen Formation and C-Proteinase

Recent evidence suggests that C-proteinase is the essential key enzyme that catalyzes the cleavage of the C-propeptide of, for example, fibrillar collagens, including type I, type II, and type III collagen. See e.g. Prockep et al., 1998, *Matrix Biol.* 16:399–408; Lee et al., 1997, *J. Biol. Chem.* 272:19059–19066; Suzuk et al., 1996, *Development* 122:3587–3595.

C-proteinase was first observed in the culture media of human and mouse fibroblasts (Goldberg et al., 1975, *Cell* 4:45–50; Kessler and Goldberg, 1978, *Anal. Biochem.* 86:463–469), and chick tendon fibroblasts (Duskin et al., 1978, *Arch. Biochem. Biophys.* 185:326–332; Leung et al., 1979, *J. Biol. Chem.* 254:224–232). An acidic proteinase which removes the C-terminal propeptides from type I procollagen has also been identified. Davidson et al., 1979, *Eur. J. Biochem.* 100:551.

A partially purified protein having C-proteinase activity was obtained from chick calvaria in 1982. Njieha et al., 1982, *Biochemistry* 23:757–764. In 1985, chicken C-proteinase was isolated, purified and characterized from conditioned media of chick embryo tendons. Hojima et al., 1985, *J. Biol. Chem.* 260:15996–16003. Murine C-proteinase has been subsequently purified from media of cultured mouse fibroblasts. Kessler et al., 1986, *Collagen Relat. Res.* 6:249–266; Kessler and Adar, 1989, *Eur. J. Biochem.* 186:115–121. Finally, the cDNA encoding human C-proteinase has been identified (see, e.g., Takahara et al., 1994, *J. Biol. Chem.* 269:26280–26285; Li et al., 1996, *Proc. Natl. Acad. Sci. USA* 93:5127–5130; Kessler et al., 1996, *Science* 271:360–362.

C-Proteinase Inhibitors

Experiments conducted with purified forms of chick and mouse C-proteinases indicate that C-proteinase is instrumental in the formation of functional collagen fibers. Fertala et al., 1994, *J. Biol. Chem.* 269:11584. As a consequence of its critical role in collagen production and maturation, scientists have sought to identify compounds that inhibit C-proteinase. See e.g., Hojima et al., supra. Compounds identified to date include metal chelators (e.g., EDTA, phenanthroline, EGTA, basic amino acids (e.g., lysine and arginine), peptides (e.g., chymostatin, pepstatin A, and concanavalin A), proteins (e.g., $\alpha_2$-macroglobulin, ovostatin, and fetal bovine serum), metals ions (e.g., $Zn^{2+}$, $Cu^{2+}$, and $Cd^{2+}$), reducing agents (e.g., dithiothreitol), detergents (e.g., sodium dodecyl sulfate (SDS)) and certain salts and buffers (e.g., phosphate, ammonium sulfate, sodium chloride and tris hydrochloride). In contrast, microbial inhibitors such as leupeptin, phosphoramidon, antipain, bestatin, elastinal, and amastatin are considered to have weak or no effect on the activity of C-proteinase. For references discussing the various C-proteinase inhibitors identified to date, see Leung et al., supra; Ryhänen et al., 1982, *Arch. Biochem. Biophys.* 215:230–236; WO97/05865; and the references cited therein.

Matrix Metalloproteinase Hydroxamic Acid Inhibitors

C-proteinase belongs to the matrix metalloproteinase (MMP) superfamily of zinc endopeptidases which are involved in tissue remodeling. Members of the MMP family include MMP-1 (human collagenase), MMP-2 (gelatinase), and MMP-9 (human gelatinase B). See e.g. WO98/34918; Krumme et al., 1998, *FEBS Lett.* 436:209–212. The MMPs are characterized by an active site zinc ion that plays an essential role in the enzymatic activity of MMPs. Rational drug discovery efforts, involving the inhibition of MMPs, have focused on inhibitor classes that contain a functional group that can coordinate the zinc ion and thereby inactivate the target MMP. See e.g. Krumme et al., supra. One such inhibitor class are hydroxamic acids. As revealed by the x-ray crystal structure determination of hydroxamic acid:MMP cocrystals, the hydroxamic acid coordinates the active site zinc in a bidentate manner via the hydroxyl and carbonyl oxygens of the hydroxamic group. See Grams et al., 1995, *Biochem.* 34:14012–14020; Bode et al., 1994, *EMBO J.*, 13:1263–1269. Despite their potent affinity as zinc coordinators, hydroxamic acids demonstrate a considerable degree of specificity within the MMP family. Thus a potent inhibitor of MMP-1 (human collagenase) may have only minimal potency against another MMP such as C-proteinase. Thus the development of potent hydroxamic acid inhibitors against a particular MMP requires considerable research effort and experimentation.

Development Of Compounds To Inhibit C-Proteinase Activity

In view of its essential role in the formation and maturation of collagen, C-proteinase provides an ideal therapeutic target towards the treatment or prevention of disorders related to, or associated with, unregulated collagen production or maturation. Accordingly, there remains a need in the art for compounds that are specific and potent inhibitors of C-proteinase, especially C-proteinase inhibitory compounds which provide clinically relevant benefits in the treatment or prevention of diseases associated with unregulated collagen production and/or maturation.

3. SUMMARY OF THE INVENTION

In one aspect, the present invention provides a novel class of organic molecules that are potent and/or selective inhibitors of C-proteinase. As a consequence of this activity, the compounds of the invention are capable of modulating, regulating or inhibiting collagen production or maturation by affecting C-proteinase activity.

The compounds of the invention are generally substituted hydantoin compounds according to structural formulae (Ia) and (Ia'):

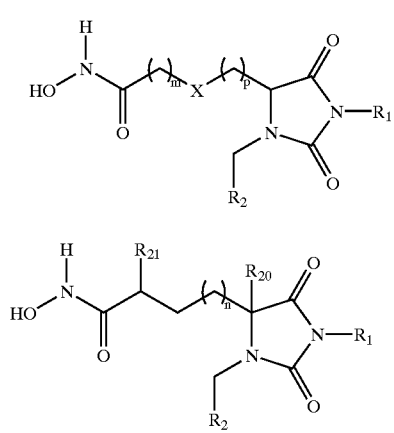

or pharmaceutically acceptable salts thereof, wherein:
m is an integer from 0 to 3 when X is $NR_{19}$ or an integer from 1 to 3 when X is S or O;

p is an integer from 1 to 4 when X is $NR_{19}$ or an integer from 1 to 3 when X is S or O;

n is and integer from 1 to 3;

X is $NR_{19}$, S or O;

$R_{19}$ is selected from the group consisting of hydrogen, $(C_1–C_5)$ alkyl, and $(C_1–C_5)$ substituted alkyl;

$R_1$ and $R_2$ are each independently selected from the group consisting of $(C_1–C_{10})$ alkyl, $(C_1–C_{10})$ substituted alkyl, $(C_3–C_{10})$ alkenyl, $(C_3–C_{10})$ substituted alkenyl, $(C_3–C_{10})$ alkynyl, $(C_3–C_{10})$ substituted alkynyl, $(C_3–C_{20})$ cycloalkyl, $(C_3–C_{20})$ substituted cycloalkyl, 3–20 membered heterocycloalkyl, 3–20 membered substituted heterocycloalkyl, $(C_5–C_{20})$ aryl, $(C_5–C_{20})$ aryl independently substituted with one or more $Y^1$, alkaryl, alkaryl independently substituted with one or more $Y^1$, 5–20 membered heteroaryl, 5–20 membered heteroaryl independently substituted with one or more $Y^1$, 6–26 membered alk-heteroaryl, and 6–26 membered alk-heteroaryl independently substituted with one or more $Y^1$;

$R_{20}$ and $R_{21}$ are each independently selected from the group consisting of hydrogen, $(C_1–C_{10})$ alkyl, $(C_6–C_{26})$ alkaryl, and 6–26 membered alk-heteroaryl; and each $Y^1$ is independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR) =NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O) (OH) (NRR), —P(O) (OH)$_{21}$, —SO$_2$R, —S(O)—R, —SO$_3$H, —SR, —SO$_2$—NRR, —OCF$_3$ and -heteroaryl; where each R is independently selected from the group consisting of, hydrogen, $(C_1–C_8)$ alkyl, $(C_3–C_8)$ alkenyl, $(C_5–C_{20})$ aryl, $(C_6–C_{26})$ alkaryl, 6–20 membered heteroaryl and 6–26-membered alk-heteroaryl;

with the proviso that the sum of m and p is 1, 2, 3 or 4.

In a preferred embodiment, the compounds of the invention iS are generally substituted hydantoin compounds having the structural formula (Ib):

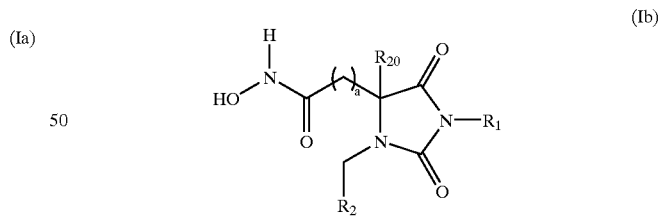

or pharmaceutically acceptable salts thereof, wherein:
a is an integer from 2 to 5; and
$R_1$, $R_2$, and $R_{20}$ are as defined for formula (Ia).

In another aspect, the present invention provides pharmaceutical compositions comprising a therapeutically effective amount of one or more of the above-described compounds and a pharmaceutically acceptable carrier, diluent or excipient. Such a composition can be used in the methods of the invention to inhibit, regulate or modulate the production or maturation of collagen by inhibiting C-proteinase activity and to treat or prevent a variety of collagen-related disorders.

In yet another aspect, the invention provides methods of inhibiting C-proteinase activity. The method involves contacting the enzyme C-proteinase, or an active fragment or derivative thereof, with an amount of a compound or composition according to the invention effective to block collagen production. Methods of inhibiting C-proteinase in vivo can be used to inhibit, regulate or modulate collagen production or maturation as a therapeutic approach towards the treatment or prevention of disorders related to, or associated with, unregulated collagen production or maturation.

In a final aspect, the present invention provides methods for the treatment or prevention of disorders related to, or associated with, inappropriate or unregulated collagen production or maturation. The method involves administering if to an animal subject, including a human, an amount of a compound according to the invention, or a pharmaceutical composition thereof, effective to treat or prevent the particular collagen-related disorder.

Disorders which can be treated or prevented according to the methods of the invention include, but are not limited to, rheumatoid arthritis, scleroderma, pathological fibrosis or scarring.

4. DEFINITIONS

As used herein, the following terms shall have the following meanings:

"C-proteinase": refers to an enzyme capable of processing collagen molecules, derivatives or fragments of collagen molecules or precursors of collagen molecules, collagen derivatives or collagen fragments by cleaving the amino acid sequence -Ala↓Asp-Asp-, -Gly↓Asp-Glu- and/or -Ala↓Asp-Gln- at the position marked with "↓". The term "C-proteinase" includes human C-proteinase as well as derivatives, analogs, fragments and variants thereof capable of processing collagen molecules as described above.

"Alkyl": refers to a saturated branched, straight chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. In preferred embodiments, the alkyl groups are $(C_1-C_8)$ alkyl, more preferably $(C_1-C_6)$ alkyl and most preferably $(C_1-C_3)$ alkyl.

"Substituted Alkyl": refers to an alkyl radical that has been substituted with one or more Q. Typical substituents Q include, but are not limited to, —X, —OR, —NRR, —N$_3$, —CN, and —CX$_3$; where each R is independently hydrogen, alkyl or substituted alkyl, and X is halogen.

"Alkenyl": refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, propenyl, isopropenyl, isopropylidene, butenyl, butenylidene, isobutenyl, tert-butenyl, cyclobutenyl, pentenyl, isopentenyl, cyclopentenyl, hexenyl, cyclohexenyl and the like. In preferred embodiments, the alkenyl group is $(C_2-C_8)$ alkenyl, more preferably $(C_2-C6)$ alkenyl and most preferably $(C_3-C_4)$ alkenyl.

"Substituted Alkenyl": refers to an alkenyl radical that has been substituted with one or more Q. Typical Q include, but are not limited to, —X, —OR, —NRR, —N$_3$, —CN, and —CX$_3$; where each R is independently hydrogen, alkyl or substituted alkyl, and X is halogen.

"Alkynyl": refers to an unsaturated branched, straight-chain or cyclic alkyl group having at least one carbon-carbon triple bond. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl , etc.; and the like. In preferred embodiments, the alkynyl group is $(C_3-C_6)$ alkynyl.

"Substituted Alkynyl": refers to an alkynyl radical that has been substituted with one or more Q. Typical Q include, but are not limited to, —X, —OR, —NRR, —N$_3$, —CN, and —CX$_3$; where each R is independently hydrogen, alkyl or substituted alkyl, and X is halogen.

"Cycloalkyl": refers to a cyclic or polycyclic saturated or unsaturated hydrocarbon radical. Typical cycloalkyl groups include, but are not limited to, cyclopropanyl, cyclobutanyl, cyclopentanyl, cyclohexanyl and higher cycloalkyls, adamantyl, cubanyl, prismanyl and higher polycylicalkyls, etc. In preferred embodiments, the cycloalkyl is $(C_3-C_{10})$ cycloalkyl. Particularly preferred cycloalkyls are cyclohexanyl and adamantyl.

"Substituted Cycloalkyl": refers to a cycloalkyl or radical wherein one or more hydrogen atoms are each independently replaced with another substituent. Typical substituents include, but are not limited to, $(C_1-C_8)$ alkyl, $(C_3-C_8)$ alkenyl, $(C_3-C_8)$ alkynyl, $(C_5-C_{20})$ aryl, $(C_6-C_{26})$ alkaryl, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen, and -trihalomethyl; where each R is independently —H, $(C_1-C_8)$ alkyl, $(C_3-C_8)$ alkenyl, $(C_3-C_8)$ alkynyl, $(C_5-C_{20})$ aryl, and $(C_6-C_{26})$ alkaryl as defined herein.

"Heterocycloalkyl": refers to a cycloalkyl moiety wherein one of the ring carbon atoms is replaced with another atom such as N, P, O, S, As, Ge, Se, Si, Te, etc. Typical heterocycloalkyls include, but are not limited to, imidazolidyl, piperazyl, piperidyl, pyrazolidyl, pyrrolidyl, quinuclidyl, etc. In preferred embodiments, the cycloheteroalkyl is 5–10 membered. Particularly preferred cycloheteroalkyls are morpholino, tetrahydrofuryl, and pyrrolidyl.

"Substituted Heterocycloalkyl": refers to a cycloheteroalkyl radical wherein one or more hydrogen atoms are each independently replaced with another substituent. Typical substituents include, but are not limited to, $(C_1-C_8)$ alkyl, $(C_3-C_8)$ alkenyl, $(C_3-C_8)$ alkynyl, $(C_5-C_{20})$ aryl, $(C_6-C_{26})$ alkaryl, 5–20 membered heteroaryl, 6–26 membered alk-heteroaryl, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl; where each R is independently —H, $(C_1-C_8)$ alkyl, $(C_2-C_8)$ alkenyl, $(C_2-C_8)$ alkynyl, $(C_5-C_{20})$ aryl, $(C6-C_26)$ alkaryl, 5–20 membered heteroaryl, and 6–26 membered alk-heteroaryl as defined herein.

"Aryl": refers to an unsaturated cyclic hydrocarbon radical having a conjugated Π electron system. Specifically included within the definition of aryls are fused ring systems in which one or more of the rings are aromatic and one or more of the rings are saturated or unsaturated, such as, for example, indane, indene, phenalene, etc. Typical aryl groups include, but are not limited to, penta-2,4-dienyl, phenyl, naphthyl, aceanthrylyl, acenaphthyl, anthracyl, azulenyl, chrysenyl, indacenyl, indanyl, ovalenyl, perylenyl, phenanthrenyl, phenalenyl, picenyl, pyrenyl, pyranthrenyl, rubicenyl and the like. In preferred embodiments, the aryl group is $(C_5-C_{20})$ aryl, more preferably $(C_5-C_{10})$ aryl and most preferably phenyl.

"Alkaryl": refers to a straight-chain or branched $(C_1-C_8)$ alkyl, $(C_2-C_8)$ alkenyl or $(C_2-C_8)$ alkynyl group wherein one of the hydrogen atoms bonded to a terminal carbon is replaced with a $(C_5-C_{20})$ aryl moiety. Typical alkaryl groups include, but are not limited to, benzyl, benzylidene, benzylidyne, benzenobenzyl, naphthalenobenzyl and the like. In preferred embodiments, the alkaryl group is ($C_6$–C26) alkaryl, i.e., the alkyl, alkenyl or alkynyl moiety of the alkaryl group is ($C_1$–$C_6$) and the aryl moiety is ($C_5$–$C_{20}$) In particularly preferred embodiments the alkaryl group is ($C_6$–$C_{13}$), i.e., the alkyl, alkenyl or alkynyl moiety of the alkaryl group is ($C_1$–$C_3$) and the aryl moiety is ($C_5$–$C_{10}$).

"Heteroaryl": refers to an aryl moiety wherein one or more carbon atoms has been replaced with another atom, such as N, P, O, S, As, Ge, Se, Si, Te, etc. Typical heteroaryl groups include, but are not limited to acridarsine, acridine, arsanthridine, arsindole, arsindoline, benzodioxole, benzothiadiazole, carbazole, β-carboline, chromane, chromene, cinnoline, furan, imidazole, indazole, indole, isoindole, indolizine, isoarsindole, isoarsinoline, isobenzofuran, isochromane, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, piazthiole, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiazopyrrolizine, thiophene and xanthene. In preferred embodiments, the heteroaryl group is a 5–20 membered heteroaryl, with 5–10 membered heteroaryl being particularly preferred.

"Alk-heteroaryl": refers to a straight-chain or branched ($C_1$–$C_8$) alkyl, ($C_2$–$C_8$) alkenyl or ($C_2$–$C_8$) alkynyl group wherein one of the hydrogen atoms bonded to a terminal carbon atom is replaced with a heteroaryl moiety. In preferred embodiments, the alk-heteroaryl group is a 6–26 membered alk-heteroaryl, i.e., the alkyl, alkenyl or alkynyl moiety of the alk-heteroaryl is ($C_1$–$C_6$) and the heteroaryl moiety is a 5–20-membered heteroaryl. In particularly preferred embodiments, the alk-heteroaryl is a 6–13 membered alk-heteroaryl, i.e., the alkyl, alkenyl or alkynyl moiety is ($C_1$–$C_3$) and the heteroaryl moiety is a 5–10 membered heteroaryl.

5. DETAILED DESCRIPTION OF THE INVENTION

The present invention provides a novel class of organic compounds capable of inhibiting the enzyme C-proteinase, pharmaceutical compositions comprising one or more of such compounds, and methods of using the compounds to inhibit, regulate or modulate collagen formation or maturation as a therapeutic approach towards the treatment or prevention of diseases related to, or associated with, unregulated collagen production or maturation.

5.1 The Compounds

In one embodiment, compounds which are capable of inhibiting C-proteinase according to the invention, and which can therefore be used in methods to inhibit, modulate or regulate collagen production or maturation or to treat or prevent diseases related to, or associated with, unregulated collagen production or maturation are generally substituted hydantoins according to structural formulae (Ia) and (Ia'):

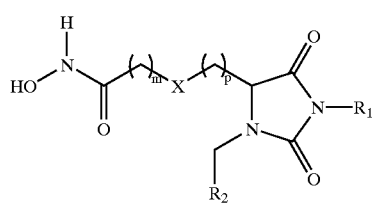

(Ia)

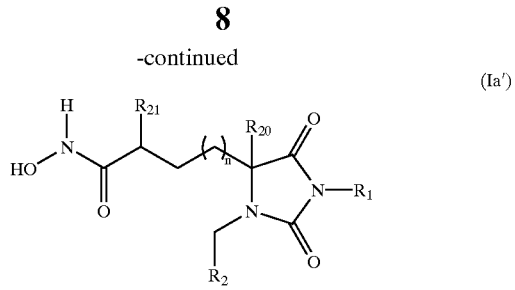

(Ia')

or pharmaceutically acceptable salts thereof, wherein:

m is an integer from 0 to 3 when X is $NR_{19}$ or an integer from 1 to 3 when X is S or O;

p is an integer from 1 to 4 when X is $NR_{19}$ or an integer from 1 to 3 when X is S or O;

n is and integer from 1 to 3;

X is $NR_{19}$, S or O;

$R_{19}$ is selected from the group consisting of hydrogen, ($C_1$–$C_5$) alkyl and ($C_1$–$C_5$) substituted alkyl;

$R_1$ and $R_2$ are each independently selected from the group consisting of ($C_1$–$C_{10}$) alkyl, ($C_1$–$C_{10}$) substituted alkyl, ($C_3$–$C_{10}$) alkenyl, ($C_3$–$C_{10}$) substituted alkenyl, ($C_3$–$C_{10}$) alkynyl, ($C_3$–$C_{10}$) substituted alkynyl, ($C_3$–$C_{20}$) cycloalkyl, ($C_3$–$C_{20}$) substituted cycloalkyl, 3–20 membered heterocycloalkyl, 3–20 membered substituted heterocycloalkyl, ($C_5$–$C_{20}$) aryl, (C5–$C_{20}$) aryl independently substituted with one or more $Y^1$, alkaryl, alkaryl independently substituted with one or more $Y^1$, 5–20 membered heteroaryl, 5–20 membered heteroaryl independently substituted with one or more $Y^1$, 6–26 membered alk-heteroaryl, and 6–26 membered alk-heteroaryl independently substituted with one or more $Y^1$;

$R_{20}$ and $R_{21}$ are each independently selected from the group consisting of hydrogen, ($C_1$–$C_{10}$) alkyl, ($C_6$–$C_{26}$) alkaryl, and 6–26 membered alk-heteroaryl; and each $Y^1$ is independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR) =NR, —NRR, —$NO_2$, —$N_3$, —NR—C(O)R, —NR—C(O)—NRR, —NR—C(O)—OR, —NR—$SO_2$—R, —NR—C(S)—NRR, —NR—C(O)R, —NR—C(O)—NRR, —NR—C(S)—NRR, —OR, —P(O) (OH) (NRR), —P(O) (OH)$_2$, —$SO_2$R, —S(O) —R, —$SO_3$H, —SR, —$SO_2$—NRR, —$OCF_3$ and -heteroaryl; where each R is independently selected from the group consisting of hydrogen, ($C_1$–$C_8$) alkyl, ($C_3$–$C_8$) alkenyl, ($C_5$–$C_{20}$) aryl, ($C_6$–$C_{26}$) alkaryl, 6–20 membered heteroaryl and 6–26-membered alk-heteroaryl;

with the proviso that the sum of m and p is 1, 2, 3 or 4.

In a preferred embodiment, the compounds of the present invention are compounds according to formula (Ia') in which $R_{20}$ and $R_{21}$ are each hydrogen and $R_1$, $R_2$, and n are as defined for formulae (Ia) and (Ia').

In another preferred embodiment, the compounds of the present invention are compounds according to formula (Ia) in which m and p are each 1. In this embodiment, X, $R_1$, and $R_2$ are as defined for formulae (Ia) and (Ia').

In still another preferred embodiment, the compounds of

In another preferred embodiment, the compounds of the present invention are compounds according to formulae (Ia) and (Ia') in which $R_1$ is cyclohexyl. In this embodiment, X, $R_{20}$, $R_{21}$, $R_2$, m, p, and n are as defined for formulae (Ia) and (Ia').

In a preferred embodiment, the compounds of the invention are generally substituted hydantoin compounds of the structural formula (Ib):

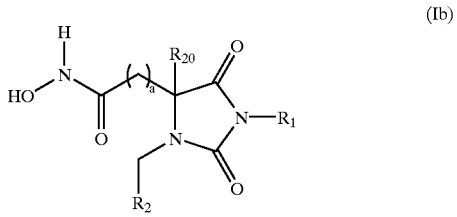

(Ib)

or pharmaceutically acceptable salts thereof, wherein:
a is 2, 3, 4, or 5; and
$R_1$, $R_2$, and $R_{20}$ are as defined for formula (Ia)

One group of preferred compounds according to formula (Ib) are those compounds having structural formula (II):

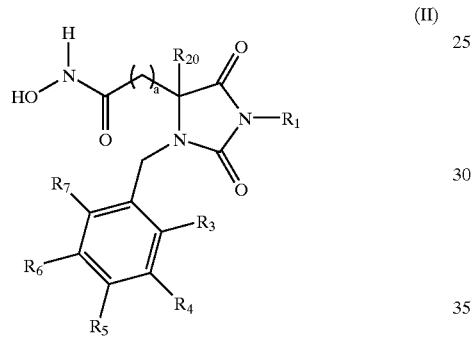

(II)

or pharmaceutically acceptable salts thereof, wherein:
a is as defined for formula (Ib);
$R_1$ and $R_{20}$ are as defined as in formula (Ia); and
$R_3$, $R_4$, $R_5$, $R_6$, and $R_7$ are each independently selected from the group consisting of -hydrogen, -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, —OCF$_3$ and -tetrazole; where each R is independently selected from the group consisting of —H, (C$_1$–C$_8$) alkyl, (C$_3$–C$_8$) alkenyl, (C$_3$–C$_8$) alkynyl, (C$_5$–C$_{20}$) aryl, (C$_6$–C$_{26}$) alkaryl, 6–20 membered heteroaryl and 6–26-membered alk-heteroaryl.

One group of preferred compounds according to formula (II) are compounds in which $R_{20}$ is hydrogen.

Another group of preferred compounds according to formula (II) are those compounds wherein a is 3. Particularly preferred compounds according to this aspect of the invention are those compounds in which $R_3$, $R_4$, $R_5$, $R_6$, and $R_7$ are each hydrogen. Particularly preferred compounds according to this aspect of the invention are compounds in which $R_{20}$ is hydrogen and $R_1$ is defined in Table 1. In Table 1, the connecting bond is dashed.

TABLE 1

| Compound # | $R_1$ |
|---|---|
| 101 | naphthyl |
| 102 | -adamantyl |
| 103 | 2,4-dichlorophenyl |
| 104 | isobutyl |
| 105 | n-pentyl |
| 106 | benzyl |
| 107 | cyclohexyl |
| 108 | neopentyl-t-butyl |
| 109 | 2-thienylethyl |

Another group of preferred compounds according to structure (Ib) are those compounds according to structural formula (III):

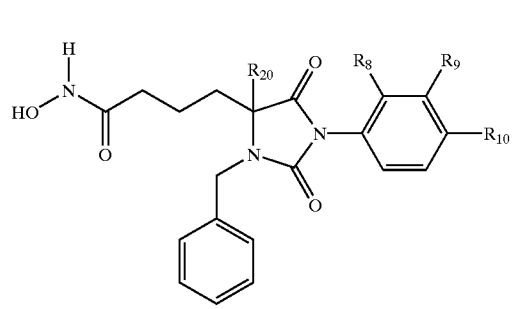

(III)

or pharmaceutically acceptable salts thereof, wherein:

$R_8$, $R_9$ and $R_{10}$ are each independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, —OCF$_3$ and -tetrazole; where each R is independently selected from the group consisting of —H, (C$_1$–C$_8$) alkyl, (C$_3$–C$_8$) alkenyl, (C$_3$–C$_8$) alkynyl, (C$_5$–C$_{20}$) aryl, (C$_6$–C$_{26}$) alkaryl, 6–20 membered heteroaryl, and 6–26-membered alk-heteroaryl; and $R_{20}$ is as defined for formula (Ia).

Particularly preferred compounds according to structure (III) are compounds in which $R_{20}$ is —H, and $R_8$, $R_9$, and $R_{10}$ are as defined in Table 2.

TABLE 2

| Compound # | $R_8$ | $R_9$ | $R_{10}$ |
|---|---|---|---|
| 110 | —H | —H | —H |
| 111 | —H | —H | —OCH$_3$ |
| 112 | —OCH$_3$ | —H | —OCH$_3$ |
| 113 | —H | —H | —NO$_2$ |
| 114 | -phenyl | —H | —H |
| 115 | —H | —H | —Cl |
| 116 | —H | —CN | —H |
| 117 | —H | —Cl | —H |
| 118 | —H | —H | —CH$_3$ |
| 119 | —H | —C(O)CH$_3$ | —H |
| 120 | —F | —H | —F |
| 121 | —Cl | —H | —Cl |
| 122 | —H | —H | -butyl |
| 123 | —H | —H | -phenoxy |
| 124 | —H | —H | -butoxy |
| 125 | —CH$_3$ | —CH$_3$ | —H |

Another group of preferred compounds according to structure (Ib) are those compounds wherein $R_1$ is adamantyl. A particularly preferred class of compounds according to this embodiment are compounds in which a is 3;

$R_2$ is selected from the group consisting of (C$_1$–C$_{10}$) alkyl, (C$_1$–C$_{10}$) substituted alkyl, (C$_3$–C$_{10}$) alkenyl, (C$_3$–C$_{10}$) substituted alkynyl, (C$_3$–C$_{10}$) alkynyl, (C$_3$–C$_{10}$) substituted alkynyl, (C$_3$–C$_{20}$) cycloalkyl, (C$_3$–C$_{20}$) substituted cycloalkyl, (C$_5$–C$_{20}$) aryl, (C$_5$–C$_{20}$) aryl independently substituted with one or more Y$^1$, alkaryl, alkaryl independently substituted with one or more Y$^1$; and Y$^1$ is as defined in structural formula (Ia); and $R_{20}$ is as defined in formula (Ia)

Particularly preferred compounds in accordance with this class of compounds are compounds in which $R_{20}$ is hydrogen and $R_2$ is as defined in Table 3. In Table 3, the connecting bond in dashed.

TABLE 3

| Compound # | $R_2$ |
|---|---|
| 126 | |
| 127 | |
| 128 | |
| 129 | |
| 130 | |
| 131 | |
| 132 | |
| 133 | |
| 134 | |

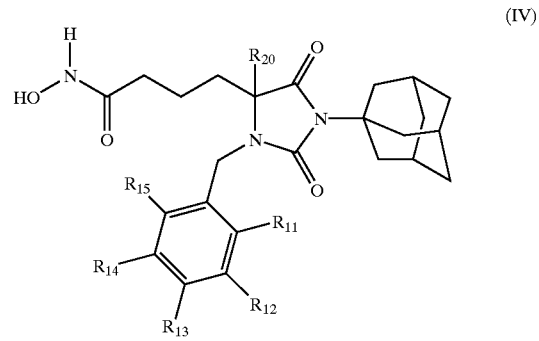

Another group of preferred compounds of the present invention are compounds according to structural formula (IV):

(IV)

or pharmaceutically acceptable salts thereof, wherein:

$R_{11}$, $R_{12}$, $R_{13}$, R14, and $R_{15}$ are each independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —N—C(O)—NRR, —NR—C(S)—

NRR, —OR, —P(O)(OH)(NRR), —P(O)(OH)$_2$, —SO$_2$R, —S(O)—R, —SR, —SO$_2$—NRR, —OCF$_3$ and -tetrazole; where each R is independently selected from the group consisting of —H, (C$_1$–C$_8$) alkyl, (C$_3$–C$_8$) alkenyl, (C$_5$–C$_{20}$) aryl, (C$_6$–C$_{26}$) alkaryl, 6–20 membered heteroaryl and 6–26-membered alkheteroaryl; and R$_{20}$ is as defined in formula (Ia).

Particularly preferred compounds according to formula (IV) are compounds in which R$_{20}$ is —H, and R$_{11}$, R$_{12}$, R$_{13}$, R$_{14}$, and R$_{15}$ as defined in Table 4:

TABLE 4

| Compound | R$_{11}$ | R$_{12}$ | R$_{13}$ | R$_{14}$ | R$_{15}$ |
|---|---|---|---|---|---|
| 135 | —H | —OCH$_3$ | —H | —OCH$_3$ | —H |
| 136 | —H | —Cl | —H | —Cl | —H |
| 137 | —H | —OH | —H | —H | —OH |
| 138 | —OH | —H | —OCH$_3$ | —H | —H |
| 139 | —H | —OCH$_3$ | —H | —H | —OH |
| 140 | —H | —Cl | —H | —H | —OH |
| 141 | —H | —OCF$_3$ | —H | —H | —OH |
| 142 | —H | —NO$_2$ | —H | —H | —OH |
| 143 | —OCH$_3$ | —H | —H | —H | —OH |
| 144 | —OCH$_3$ | —H | —H | —H | —OCH$_3$ |
| 145 | —H | —OH | —H | —OH | —H |
| 146 | —H | —Br | —H | —OCH$_3$ | —OH |

A group of preferred compounds according to formula (IV) are those compounds in which R$_{14}$ and R$_{15}$ are hydrogen. Particularly preferred compounds according to this class of compounds are compounds in which R$_{20}$ is hydrogen and R$_{11}$, R$_{12}$, and R$_{13}$ are as in Table 5.

TABLE 5

| Compound # | R$_{11}$ | R$_{12}$ | R$_{13}$ |
|---|---|---|---|
| 102 | —H | —H | —H |
| 148 | —H | —H | —Cl |
| 149 | —H | —H | —OCH$_3$ |
| 150 | —H | —H | -phenyl |
| 151 | —H | —H | —N(CH$_3$)$_2$ |
| 152 | —H | —H | —NO$_2$ |
| 153 | —H | —H | -phenoxy |
| 154 | —H | —H | —F |
| 155 | —OH | —H | —H |
| 156 | —H | —H | —CF$_3$ |
| 157 | —H | —H | —OH |
| 158 | —H | —H | —CH$_3$ |
| 159 | —H | —OCH$_3$ | —OCH$_3$ |
| 160 | —F | —H | —F |
| 161 | —H | —OH3 | —H |
| 162 | —OCH$_3$ | —OCH$_3$ | —H |
| 163 | —OCH$_3$ | —H | —H |
| 164 | —OH | —H | —OH |
| 165 | —NO$_2$ | —H | —H |
| 166 | —H | —OH | —OCH$_3$ |
| 167 | —OH | —OH | —H |
| 168 | —OH | —OCH$_3$ | —H |
| 169 | —COOH | —H | —H |
| 170 | —H | —CH$_3$ | —H |
| 171 | —H | —OCH$_3$ | —H |
| 172 | —H | —Cl | —H |
| 173 | —H | —COOH | —H |

A group of preferred compounds according to formula (Ib) are those compounds in which R$_2$ is selected from the group consisting of 5–20 membered heteroaryl, 5–20 membered heteroaryl independently substituted with one or more Y$^1$, 3–20 membered heterocycloalkyl, 3–20 membered substituted heterocycloalkyl, 2–26 membered alk-heteroaryl, and 6–26 membered alk-heteroaryl independently substituted with one or more Y$^1$; and Y$^1$ is as defined in formula (Ia).

Particularly preferred compounds according to this embodiment are compounds in which a is 3, R$_{20}$ is —H, and R$_1$ is adamantyl. Preferred compounds in this class include compounds of Table 6. In Table 6, the connecting bond is dashed.

TABLE 6

| Compound # | R$_2$ |
|---|---|
| 174 | 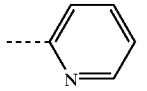 |
| 175 | 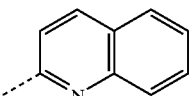 |
| 176 | 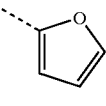 |
| 177 | 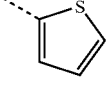 |
| 178 | 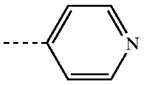 |
| 179 | 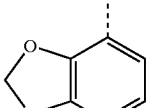 |
| 180 | 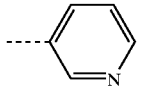 |
| 181 | 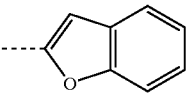 |
| 182 | 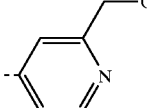 |
| 183 | 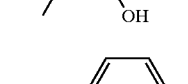 |
| 184 |  |
| 185 | 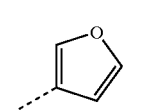 |

TABLE 6-continued

| Compound # | R₂ |
|---|---|
| 186 | benzyl |
| 187 | N-methylpyrrol-2-yl |
| 188 | thiazol-2-yl |
| 189 | 3,5-dimethylfuran-2-yl |
| 190 | 5-(3-nitrophenyl)furan-2-yl |
| 191 | indol-3-yl |
| 192 | 3,4-dihydro-2H-pyran-6-yl |

Another group of preferred compounds according to structural formula (Ib) are those compounds wherein $R_1$ is cyclohexyl. Particularly preferred compounds according to this aspect of the invention are those compounds in which a is 3. Even more preferred are compounds in this embodiment in which $R_{20}$ is hydrogen and $R_2$ is as defined in Table 7. In Table7, the connecting bond is dashed.

TABLE 7

| Compound # | R₂ |
|---|---|
| 107 | phenyl |
| 194 | pyridin-2-yl |
| 195 | 2-hydroxyphenyl |

TABLE 7-continued

| Compound # | R₂ |
|---|---|
| 196 | furan-2-yl |
| 197 | benzo[1,3]dioxol-4-yl |
| 198 | 3-hydroxyphenyl |

Yet another group of preferred compounds according to formula (Ia) are those compounds in which X is S. Particularly preferred compounds in which X is S are those compounds in which m is 1, p is 1 and $R_1$ is adamantyl. Of the compounds of this class, compound 199 is particularly preferred:

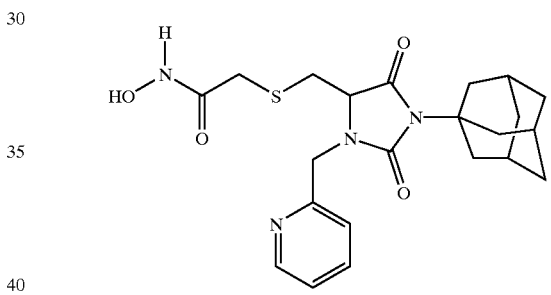

Another group of preferred compounds according to formula (Ia) are those compounds in which X is $NR_{19}$. Particularly preferred compounds in this embodiment are those compounds in which m is 0, p is 3, and $R_1$ is adamantyl. A particularly preferred compound in this embodiment is compound 200:

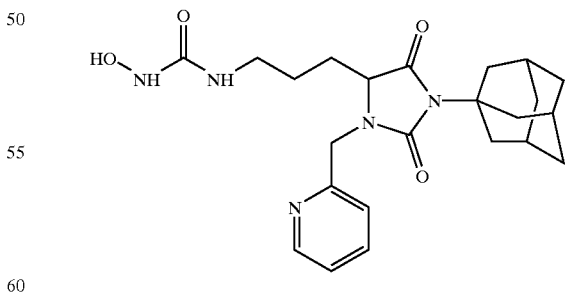

Another group of preferred compounds according to formula (Ia) are those compounds in which X is O.

A group of preferred compounds according to formula (Ia') are those compounds in which $R_1$ is cyclohexyl, $R_{20}$ and $R_{21}$ are each methyl and $R_2$ is as defined in Table 8. In Table 8, the connecting bond is dashed.

TABLE 8

| Compound # | R$_2$ |
|---|---|
| H1 | phenyl |
| H2 | pyridin-2-yl |
| H3 | 2-hydroxyphenyl |
| H4 | furan-2-yl |
| H5 | benzo[1,3]dioxol-4-yl |
| H6 | 3-hydroxyphenyl |

Another group of preferred compounds according to formula (Ia') are those compounds in which R$_1$ is adamantyl, R$_{20}$ and R$_{21}$ are each methyl and R$_2$ is as defined in Table 9. In Table 9, the connecting bond is dashed.

TABLE 9

| Compound # | R$_2$ |
|---|---|
| H7 | pyridin-2-yl |
| H8 | quinolin-2-yl |
| H9 | furan-2-yl |
| H10 | thiophen-2-yl |
| H11 | pyridin-4-yl |
| H12 | benzo[1,3]dioxol-4-yl |
| H13 | pyridin-3-yl |
| H14 | benzofuran-2-yl |
| H15 | 6-(hydroxymethyl)-3-methyl-2-hydroxypyridin-4-yl |
| H16 | 5-(hydroxymethyl)furan-2-yl |
| H17 | 5-ethylfuran-2-yl |
| H18 | furan-3-yl |
| H19 | 1H-pyrrol-2-yl |
| H20 | 1-methyl-1H-pyrrol-2-yl |
| H21 | thiazol-2-yl |
| H22 | 4,5-dimethylfuran-2-yl |
| H23 | 5-(3-nitrophenyl)furan-2-yl |

TABLE 9-continued

| Compound # | R₂ |
|---|---|
| H24 | *(3-indolyl group)* |
| H25 | *(3,4-dihydro-2H-pyran-6-yl group)* |

The chemical structural formulae referred to herein may exhibit the phenomena of tautomerism, conformational isomerism, geometric isomerism and/or stereo isomerism. As the formulae drawings within this specification can only represent one of the possible tautomeric, conformational isomeric, geometric isomeric or stereo isomeric forms, it should be understood that the invention encompasses any tautomeric, conformational isomeric, geometric isomeric or stereo isomeric forms which exhibit biological or pharmacological activity as defined herein.

The compounds of the invention may be in the form of free acids, free bases or pharmaceutically effective acid addition or base addition salts. Such acid addition salts can be readily prepared by treating a compound with a pharmaceutically acceptable acid. Pharmaceutically acceptable acids include, by way of example and not limitation, inorganic acids such as hydrohalic acids (hydrochloric, hydrobromic, etc.), sulfuric acid, nitric acid, phosphoric acid, etc.; and organic acids such as acetic acid, propanoic acid, 2-hydroxyacetic acid, 2-hydroxypropanoic acid, 2-oxopropanoic acid, propandioic acid, butandioic acid, etc. Conversely, the acid addition salt can be converted into the free base form by treatment with alkali. Appropriate base addition salts can be readily prepared by treating a compound with a pharmaceutically acceptable base.

In addition to the above compounds and their pharmaceutically acceptable salts, the invention is further directed, where applicable, to solvated as well as unsolvated forms of the compounds (e.g. hydrated forms) exhibiting biological or pharmacological activity as defined herein.

5.2 Methods of Making the Compounds

The compounds of the invention may be prepared by any process known to be applicable to the preparation of chemical compounds. Suitable processes are well-known in the art. Preferred processes are illustrated by the representative examples. Necessary starting materials may be obtained commercially or by standard procedures of organic chemistry.

By way of example, the compounds of the invention can be conveniently prepared by schemes (I) thru (XII) below:

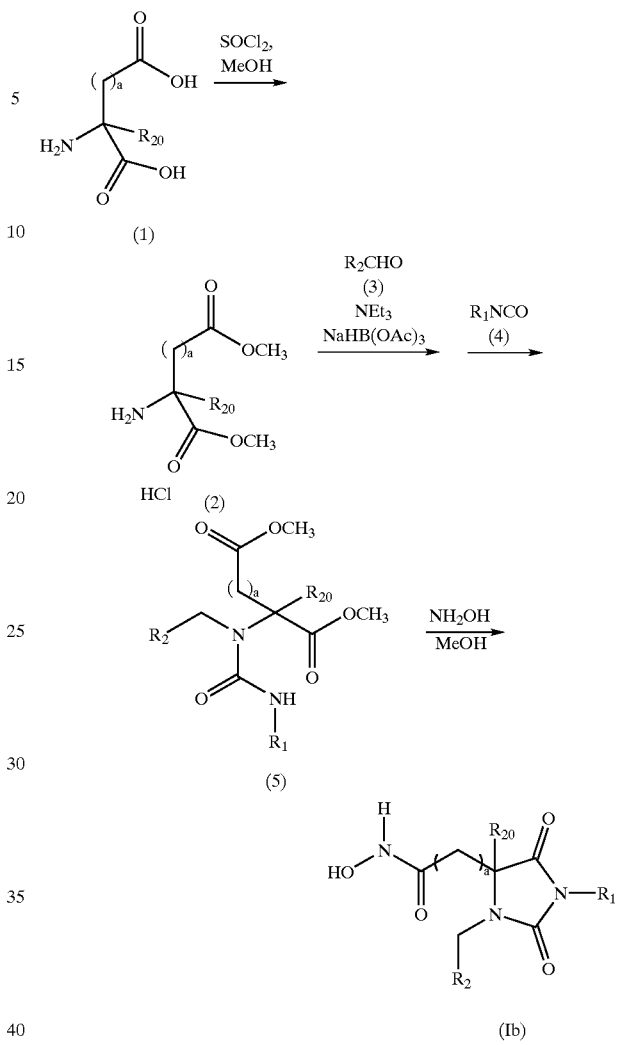

In Scheme (I), compounds of formula (Ib) are synthesized and a, $R_1$, $R_2$, and $R_{20}$ are as defined for formula (Ib).

According to scheme (I), D,L-2-amino-($C_2$–$C_5$) alkanedioic acid 1 was mixed with $SOCl_2$ in MeOH to yield D,L-2-amino-($C_2$–$C_5$)alkanedioic acid dimethyl ester hydrochloride 2. To compound 2 (0.5 mM) in $CH_2Cl_2$ (5 mL) was added triethylamine to (0.55 mM), aldehyde 3 (0.55 mM), and sodium triacetoxyborohydride (0.7 mM). The reaction mixture was shaken at room temperature for six hours, and then isocynate 4 (0.55 mM) was added. The mixture was shaken for an additional twelve hours and then quenched with 1 mL of 1 N HCl. The organic phase was washed with water (5 mL), dried over $MgSO_4$, filtered, and concentrated to yield residue 5. Residue 5 was treated with freshly prepared hydroxylamine solution (1.5 mL, 1.5 mM) for twelve hours, and then quenched with 2 mL of 1N HCl, and 6 ml of $CH_2Cl_2$. The organic phase was washed with water (5 mL), dried over $MgSO_4$, filtered and concentrated to yield compound of formula (Ib). Compound of formula (Ib) was triturated in ether/hexane (1.1, 5 mL), and dried in vaccuo.

D,L-2-amino-($C_2$–$C_5$)alkanedioic acid compounds 1 in which $R_{20}$ is hydrogen are commercially available. Compounds 1 in which $R_{20}$ is a ($C_1$–$C_{10}$) alkyl, (C6–$C_{26}$) alkaryl, and 6–26 membered alk-heteroaryl are synthesized by Strecker synthesis as follows:

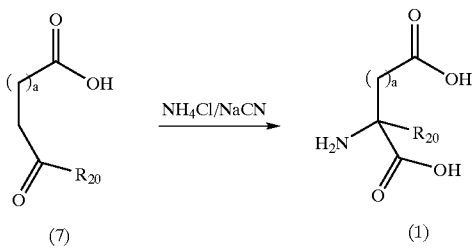

See, for example, Gal et al., 1954, J. Am. Chem. Soc. 76, 4181, Izumi et al., 1965, Bull. Chem. Soc. Jpn., 38, 1338, Weinges et al., 1971, Chem. Ber., 104, 3594.

SCHEME (II)

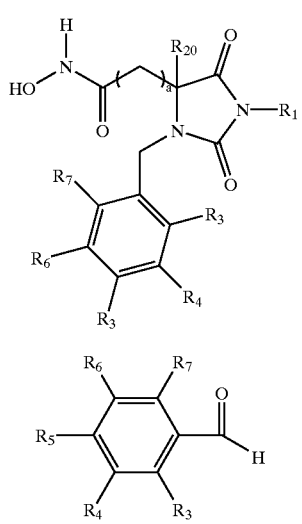

In Scheme (II), compounds of formula (II) are synthesized. Accordingly, $R_1$, $R_3$, $R_4$, $R_5$, $R_6$, $R_7$, $R_{20}$ and a are as defined in formula (II). Compounds of Scheme (II) are synthesized according to Scheme (I) by using compound 10 for aldehyde 3.

SCHEME (III)

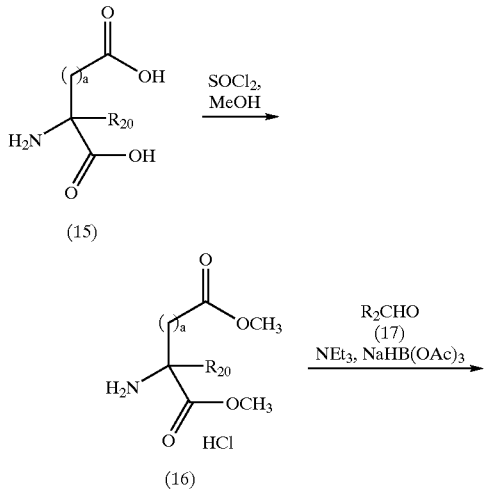

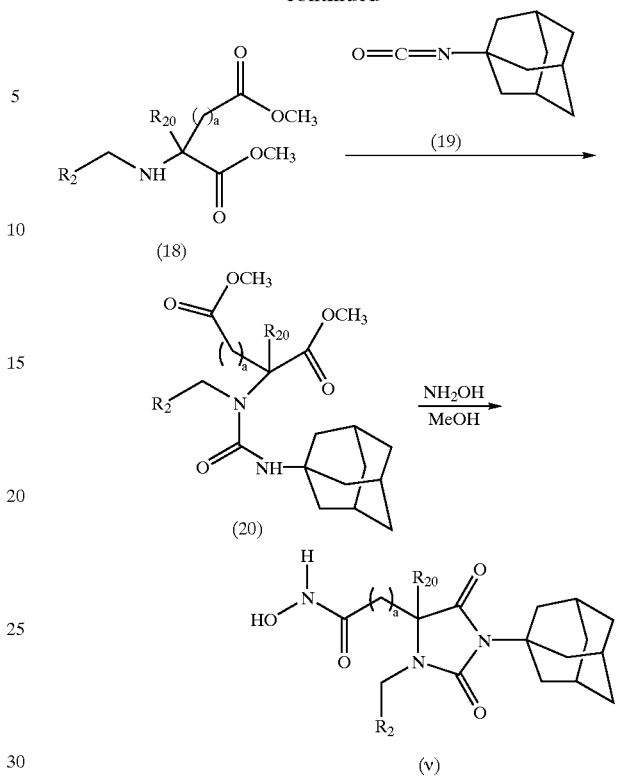

In Scheme (III), a, and $R_{20}$ are as defined for formula (Ib). $R_2$ is selected from the group consisting of $(C_1-C_{10})$ alkyl, $(C_1-C_{10})$ substituted alkyl, $(C_3-C_{10})$ alkenyl, $(C_3-C_{10})$ substituted alkenyl, $(C_3-C_{10})$ alkynyl, $(C_3-C_{10})$ substituted alkynyl, $(C_3-C_{20})$ cycloalkyl, $(C_3-C_{20})$ substituted cycloalkyl, $(C_5-C_{20})$ aryl, $(C_5-C_{20})$ aryl independently substituted with one or more $Y^1$, alkaryl, alkaryl independently substituted with one or more $Y^1$; where $Y^1$ is as defined in structural formula (Ia). According to Scheme (III), D,L-2-amino-$(C_2-C_5)$ alkanedioic acid 15 was mixed with $SOCl_2$ in MeOH to yield D,L-2-amino-$(C_2-C_5)$alkanedioic acid dimethyl ester hydrochloride 16. To compound 16 (0.5 mM) in $CH_2Cl_2$ (5 mL) was added triethylamine (0.55 mM), aldehyde 17 (0.55 mM), and sodium triacetoxyborohydride (0.7 mM). The reaction mixture was shaken at room temperature for six hours, and then adamantyl-isocynate 19 (0.55 mM) was added. The mixture was shaken for an additional twelve hours, and then quenched with 1 mL of 1 N HCl. The organic phase was washed with water (5 mL), dried over $MgSO_4$, filtered, concentrated and dried to yield residue 20. Residue 20 was treated with freshly prepared hydroxylamine solution (1.5 mL, 1.5 mM) for twelve hours, and then quenched with 2 mL of 1N HCl, and 6 ml of $CH_2Cl_2$. The organic phase was washed with water (5 mL), dried over $MgSO_4$, filtered and concentrated to yield compound of formula (V). Compound of formula (V) was triturated in ether/hexane (1.1, 5 mL), and dried in vaccuo.

D,L-2-amino-$(C_2-C_5)$ alkanedioic acid compounds 15 in which $R_{20}$ is hydrogen are commercially available. Compounds 15 in which $R_{20}$ is other than hydrogen may be prepared by Strecker synthesis as described in Scheme (I).

SCHEME (IV)

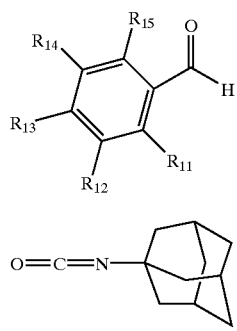

(25)

(27)

In Scheme (IV), compounds of formula (IV) are synthesized. Accordingly, a, $R_{11}$, $R_{12}$, $R_{13}$, $R_{14}$, and $R_{15}$ and $R_{20}$ are as defined in formula (IV). Compounds are synthesized as described in Scheme (I) by using aldehyde 25 for compound 3 and Adamantyl-isocynate 27 for compound 4.

SCHEME (V)

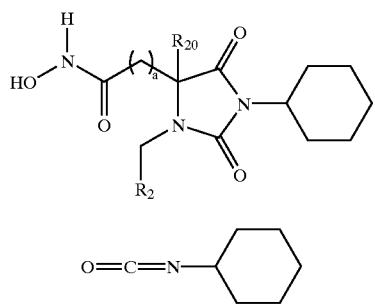

(37)

(35)

In Scheme (V), a, $R_{20}$, and $R_2$ are as defined in formula (Ib). In Scheme (V), compounds 37 are synthesized using the synthesis described in Scheme (I), where cyclohexyl-isocynate 35 is used for compound 4.

SCHEME (VI)

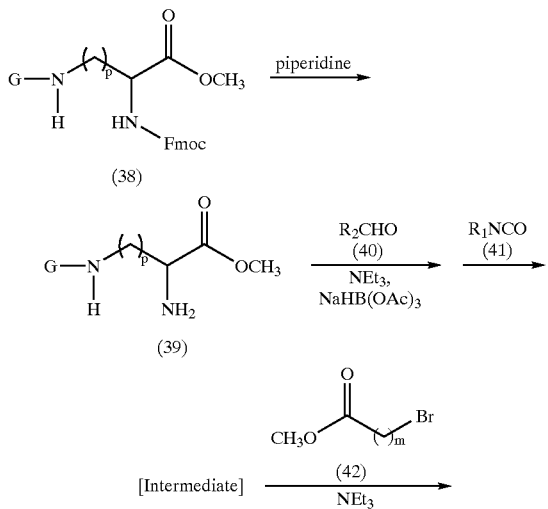

(38)

(39)

[Intermediate]

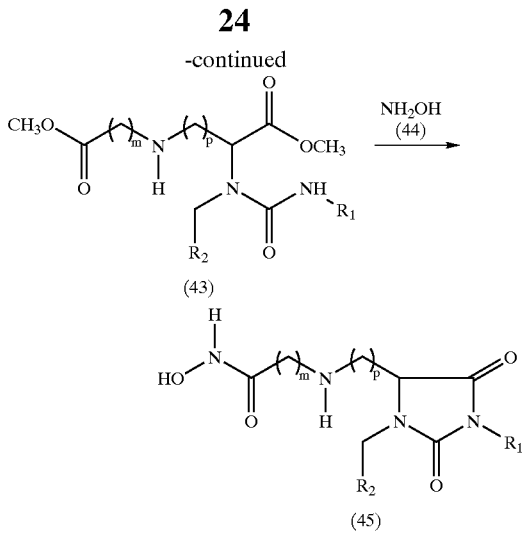

(43)

(45)

In Scheme (VI), $R_1$, $R_2$, m, and p are as defined in formula (Ia) and Fmoc is 9-fluorenylmethyl carbamate. Suitable amino protecting groups, G, may be found, for example, in Greene & Wuts, 1991, *Protective Groups in Organic Synthesis*, John Wiley & Sons, New York. In a preferred embodiment, G is tert-butoxycarbonyl.

According to Scheme (VI), compounds of formula (Ia) in which X is NH are synthesized. Compound 38 was mixed with piperidine to yield compound 39. To compound 39 (O.5 mM) in $CH_2Cl_2$ (5 mL) was added triethylamine (0.55 mM), aldehyde 40 (0.55 mM), and sodium triacetoxyborohydride (0.7 mM). The reaction mixture was shaken at room temperature for six hours, and then isocynate 41 (0.55 mM) was added. The mixture was shaken for an additional twelve hours and then quenched with 1 N HCl. The organic phase was washed with water (5 mL), dried over $MgSO_4$, filtered, and concentrated to yield intermediate. Intermediate, in which the protecting group G was tert butoxycarbonyl, was treated with trifluoroacetic acid in $CH_2Cl_2$ (5 percent, 5 mL) for five hours and then concentrated. The resulting residue was dissolved in 5 mL of $CH_2Cl_2$ and triethylamine and compound 42 were added. The mixture was stirred for twelve hours at room temperature. The reaction mixture was concentrated and purified by silica gel chromatography to give residue 43. Residue 43 was treated with freshly prepared hydroxylamine solution (1.5 mL, 1.5 mM) 44 for twelve hours, and then quenched with 2 mL of 1N HCl, and 6 mL of $CH_2Cl_2$. The organic phase was washed with water (5 mL), dried over $MgSO_4$, filtered and concentrated to yield compound 45.

SCHEME (VII)

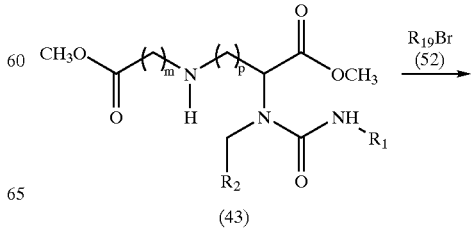

(43)

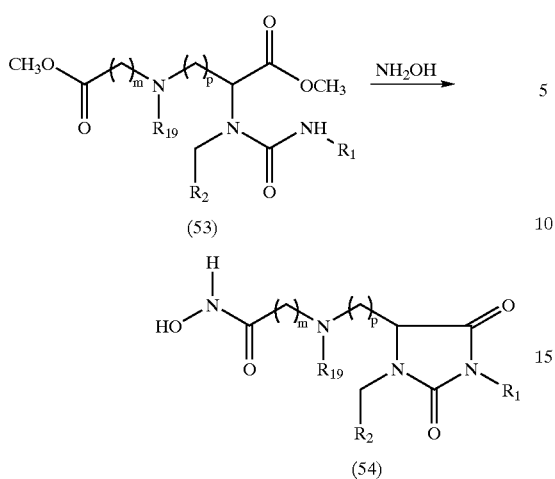

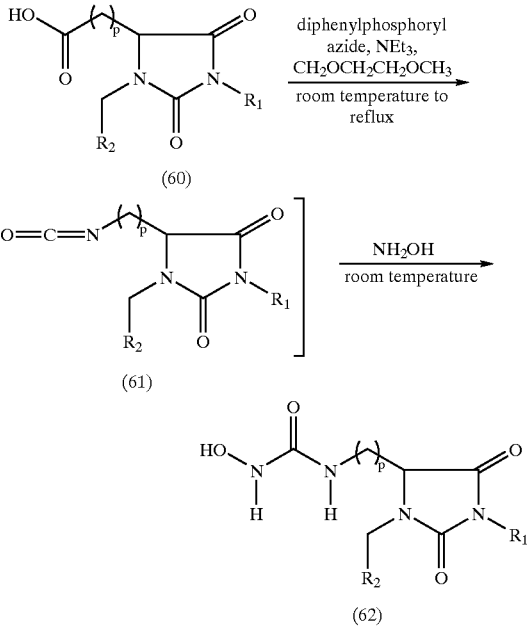

In Scheme (VII), compounds of formula (Ia) in which X is $NR_{19}$ are synthesized. Accordingly, m, p, $R_1$, $R_2$, and $R_{19}$ are as defined in formula (Ia). According to Scheme (VII), compound 43, which was synthesized as detailed in Scheme (VI), was mixed with compound 52 to yield compound 53. Compound 53 was treated with freshly prepared hydroxylamine solution (1.5 mL, 1.5 mM) for twelve hours, and then quenched with 2 mL of 1N HCl, and 6 mL of $CH_2Cl_2$. The organic phase was washed with water (5 mL), dried over $MgSO_4$, filtered and concentrated to yield 54.

SCHEME (VIII)

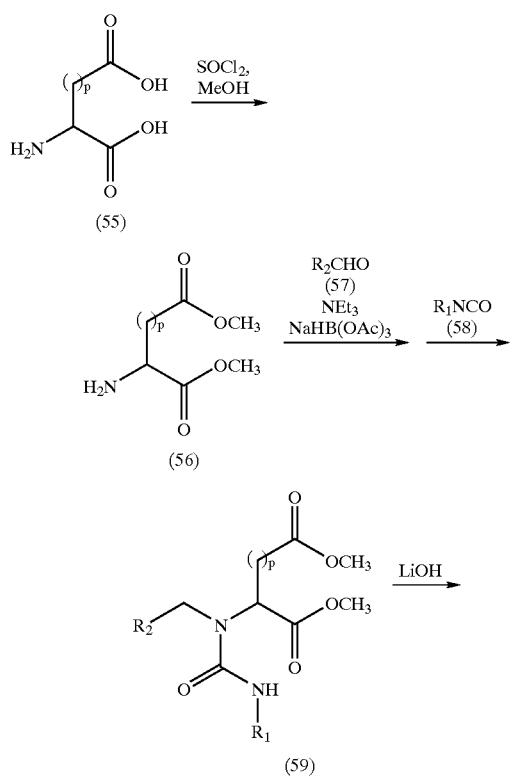

In Scheme (VIII), compounds of formula (Ia) in which X is NH are synthesized. Accordingly, p, $R_1$ and $R_2$ are as defined in formula (Ia). According to Scheme (VIII), D,L-2-amino-($C_2$–$C_5$) alkanedioic acid 55 is mixed with $SOCl_2$ in MeOH to yield D,L-2-amino-($C_2$–$C_5$)alkanedioic acid dimethyl ester hydrochloride 56. To compound 56 (0.5 mM) in $CH_2Cl_2$ (5 mL) was added triethylamine (0.55 mM), aldehyde 57 (0.55 mM), and sodium triacetoxyborohydride (0.7 mM). The reaction mixture was shaken at room temperature for six hours, and then isocynate 58 (0.55 mM) was added. The mixture was shaken for an additional twelve hours and then quenched with 1 mL of 1 N HCl. The organic phase was washed with water (5 mL), dried over $MgSO_4$, filtered, concentrated and dried to yield residue 59. Residue 59 was treated with LiOH to yield compound 60. Compound 60 was mixed with diphenylphosphoryl azide, triethylamine, and ethylene glycol and refluxed at room temperature to form isocyanate 61. Isocyanate 61 was treated with freshly prepared hydroxylamine solution (1.5 mL, 1.5 mM) for twelve hours, and then quenched with 2 mL of 1N HCl, and 6 mL of $CH_2Cl_2$. The organic phase was washed with water (5 mL), dried over $MgSO_4$, filtered and concentrated to yield N-hydroxy-urea 62.

SCHEME (IX)

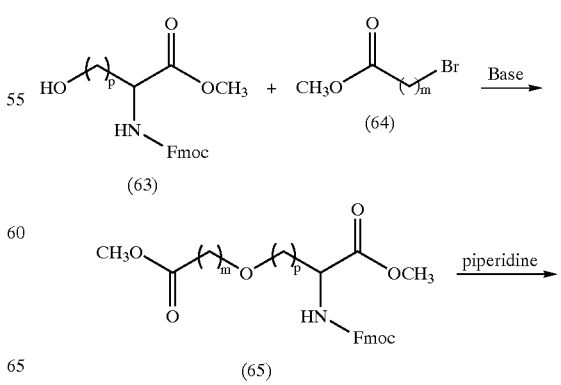

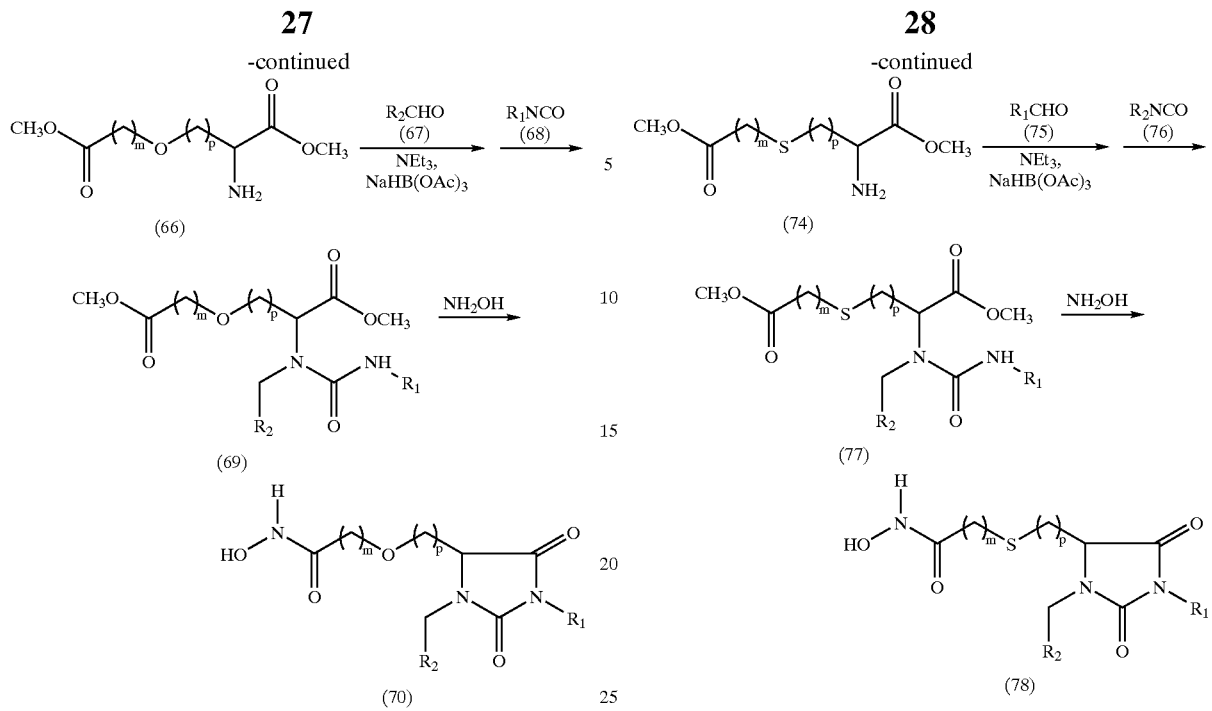

In Scheme (IX), compounds of formula (Ia) in which X is O are synthesized. Accordingly, $R_1$, $R_2$, m, and p are as defined for formula (Ia) and Fmoc is 9-fluorenylmethyl carbamate. According to Scheme (IX), Compound 63 was combined with compound 64 in the presence of a base to yield compound 65. One suitable base was sodium hydride. Compound 65 was deprotected using piperidine to yield the corresponding free amine 66. Additionally, deprotection of the Fmoc group of compound 65 may be effected by the use of other amine bases as described in Greene and Wuts, supra, pages 318–319. To compound 66 (0.5 mM) in $CH_2Cl_2$ (5 mL) was added triethylamine (0.55 mM), aldehyde 67 (0.55 mM), and sodium triacetoxyborohydride (0.7 mM). The reaction mixture was shaken at room temperature for six hours, and then isocynate 68 (0.55 mM) is added. The mixture was shaken for an additional twelve hours and then quenched with 1 mL of 1 N HCl. The organic phase was washed with water (5 mL), dried over $MgSO_4$, filtered, and concentrated to yield residue 69. Residue 69 was treated with freshly prepared hydroxylamine solution (1.5 mL, 1.5 mM) for twelve hours, and then quenched with 2 mL of 1N HCl, and 6 ml of $CH_2Cl_2$. The organic phase was washed with water (5 mL), dried over $MgSO_4$, filtered and concentrated to yield residue 70. Residue 70 was triturated in ether/hexane (1.1, 5 mL), and dried in vaccuo.

SCHEME (X)

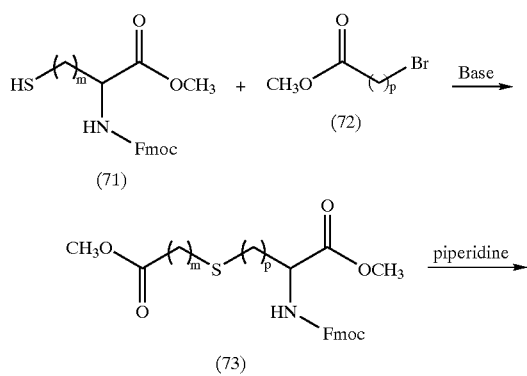

In Scheme (X), compounds of formula (Ia) in which X is S are synthesized. Accordingly, $R_1$, $R_2$, m and p are as defined for formula (Ia) and Fmoc is 9-fluorenylmethyl carbamate.

According to Scheme (X), compound 71 was combined with compound 72 in the presence of a base to yield compound 73. One suitable base was sodium hydride. Compound 73 was deprotected using piperidine to yield the corresponding free amine 74. Additionally, deprotection of the Fmoc group of compound 74 may be effected by the use of other amine bases as described in Greene and Wuts, supra, pages 318–319. To compound 74 (0.5 mM) in $CH_2Cl_2$ (5 mL) was added triethylamine (0.55 mM), aldehyde 75 (0.55 mM), and sodium triacetoxyborohydride (0.7 mM). The reaction mixture was shaken at room temperature for six hours, and then isocynate 76 (0.55 mM) was added. The mixture was shaken for an additional twelve hours and then quenched with 1 mL of 1 N HCl. The organic phase was washed with water (5 mL), dried over $MgSO_4$, filtered, concentrated and dried to yield residue 77. Residue 77 was treated with freshly prepared hydroxylamine solution (1.5 mL, 1.5 mM) for twelve hours, and then quenched with 2 mL of 1N HCl, and 6 ml of $CH_2Cl_2$. The organic phase was washed with water (5 mL), dried over $MgSO_4$, filtered and concentrated to yield residue 78. Residue 78 was triturated in ether/hexane (1.1, 5 mL), and dried in vaccuo.

SCHEME (XI)

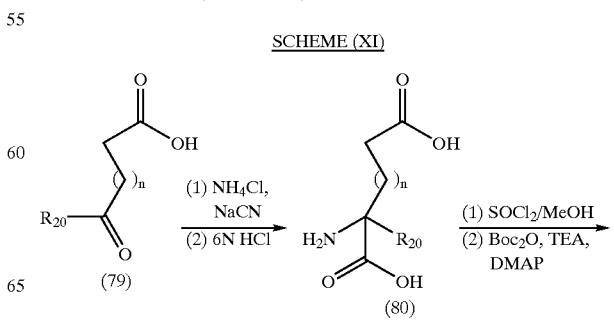

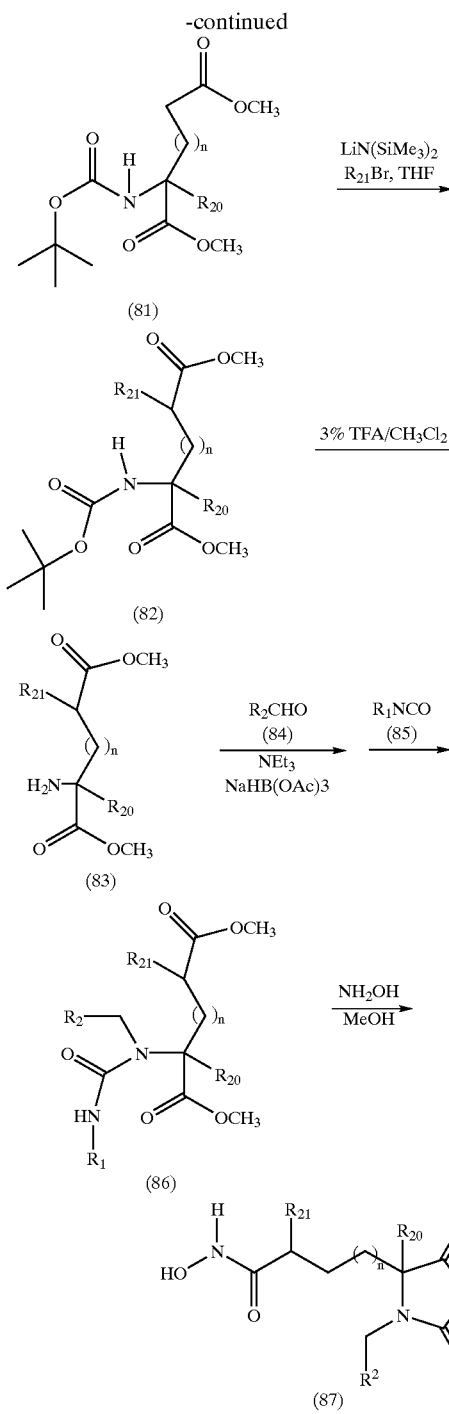

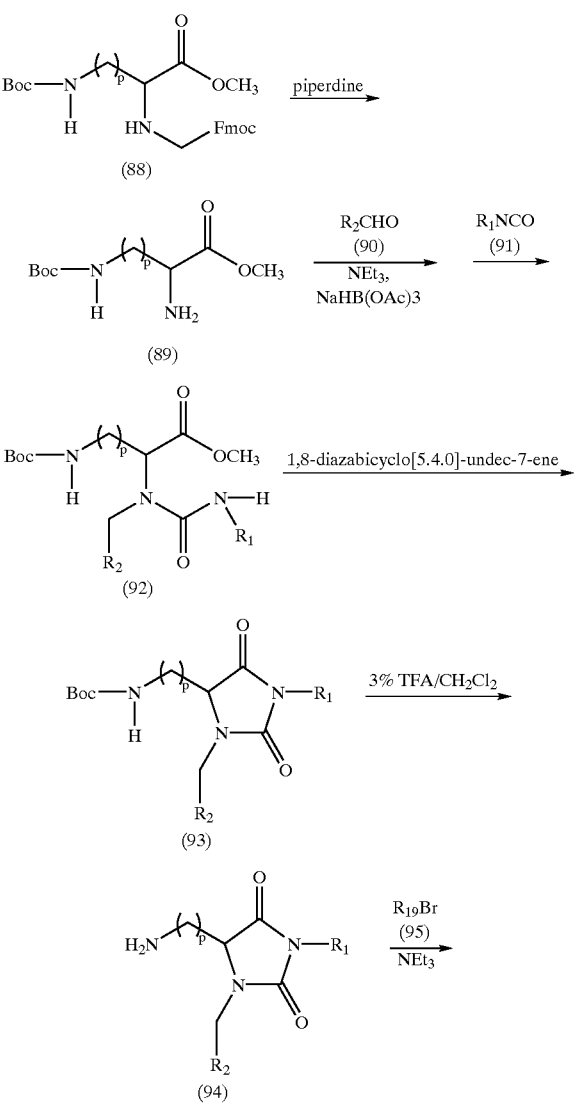

treating with lithium hexamethyldisilylamide [LiN(SiMe$_3$)$_2$], followed by the addition of R$_{21}$Br to give compound 82. The Boc (tert-butylcarbonate) protecting group of compound 82 was removed by treating with three percent trifluoroacetic acid (TFA) in methylene chloride to furnish compound 83. To compound 83 (0.5 mM) in CH$_2$Cl$_2$ (5 mL) was added triethylamine (0.55 mM), aldehyde 84 (0.55 mM), and sodium triacetoxyborohydride (0.7 mM). The reaction mixture was shaken at room temperature for six hours, and then isocynate 85 (0.55 mM) was added. The mixture was shaken for an additional twelve hours and then quenched with 1 mL of 1 N HCl. The organic phase was washed with water (5 mL), dried over MgSO$_4$, filtered, and concentrated to yield residue 86. Residue 86 was treated with freshly prepared hydroxylamine solution (1.5 mL, 1.5 mM) for twelve hours, and then quenched with 2 mL of 1N HCl, and 6 ml of CH$_2$Cl$_2$. The organic phase was washed with water (5 mL), dried over MgSO$_4$, filtered and concentrated to yield residue 87. Residue 87 was triturated in ether/hexane (1.1, 5 mL), and dried in vaccuo.

In Scheme (XI), compounds of formula (Ia') are synthesized. Accordingly, R$_1$, R$_2$, R$_{20}$, R$_{21}$, and n are as defined in formula (Ia'). According to scheme (XI), D,L-2-amino-(C$_2$–C$_5$)alkanedioic acid 80 is prepared by Strecker synthesis from compound 79. See, for example, Gal et al., 1954, J. Am. Chem. Soc. 76, 4181, Izumi et al., 1965, Bull. Chem. Soc. Jpn., 38, 1338, Weinges et al., 1971, Chem. Ber., 104, 3594. Compound 80 is mixed with SOCl$_2$ in MeOH to yield D,L-2-amino-(C$_2$–C$_5$)alkanedioic acid dimethyl ester hydrochloride, the amino group of which was protected by tert-butylcarbamate (Boc) by reacting with Boc$_2$O in the presence of triethylamine (TEA) and demethylaminopyridine (DMAP) to yield 81. Compound 81 was enolated by -continued

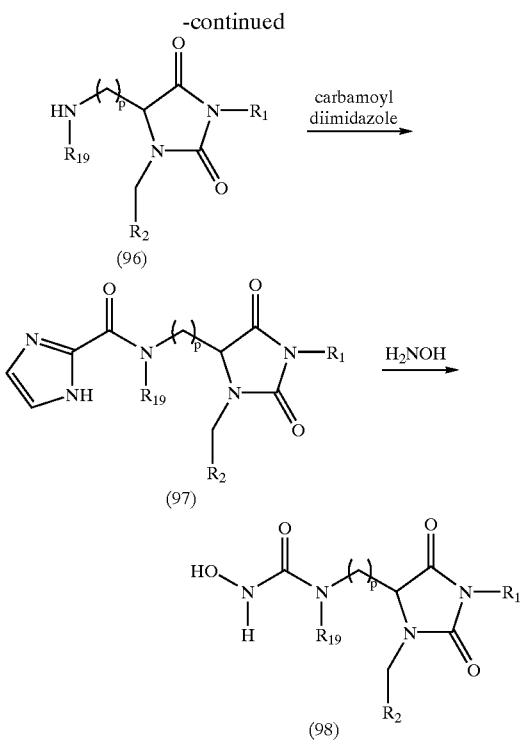

In Scheme (XII), compounds of formula (Ia) in which X is $NR_{19}$ and m is 0 are synthesized. Accordingly, $R_1$, $R_2$ and p are as defined in formula (I).

According to Scheme (XII), compound 88 is mixed with piperidine to yield compound 89. To compound 89 (0.5 mM) in $CH_2Cl_2$ (5 mL) is added triethylamine (0.55 mM), aldehyde 90 (0.55 mM), and sodium triacetoxyborohydride (0.7 mM). The reaction mixture is shaken at room temperature for 6 hours, and then isocyanate 91 (0.55 mM) is added. The mixture is shaken for additional 12 hours and the quenched with 1 N HCl. The organic phase is washed and dried to yield 92. The cyclization of compound 92 is carried out in the presence of 1,8-diazabicyclo[5.4.0]undec-7-ene to afford 93. Tert-butoxycarbonyl (Boc) protecting group is removed upon treatment with 3% trifluoroacetic acid (TFA)/$CH_2Cl_2$ to provide compound 94, which, after being concentrated several times in ether, in turn reacts with 95 to yield compound 96. Compound 96 is then reacted with carbonyl diimidazole to give compound 97. Compound 97 is treated with freshly prepared hydroxylamine solution to yield compound 98.

5.3 Biological and Pharmacological Activity

An individual compound's relevant activity and potency as an inhibitor of C-proteinase, to regulate or modulate collagen production or maturation and/or to treat disorders associated with unregulated collagen production may be determined using available techniques.

Typically, active compounds of the invention will inhibit 50% of the activity of C-proteinase at concentrations in the range of 100 micromolar ($\mu M$) or less (i.e., those compounds exhibiting an $IC_{50}$ of 100 $\mu M$ or less) using standard biochemical assays Dickson, 1953, Biochem. J. 55:170–171; Knight et al., 1992, FEBS 296:263–266. Those of skill in the art will appreciate that compounds exhibiting lower inhibitory concentrations ($IC_{50}$s) are generally preferred for pharmacological applications; thus, preferably active compounds will exhibit $IC_{50}$s that are less than 10 $\mu M$, more preferably less than 1 $\mu M$, even more preferably less than 100 nanomolar (nM) and even more preferably less than about 10 nM or 1 nM. However, as compounds which exhibit $IC_{50}$s in the millimolar (mM) range can provide consequential pharmacological benefits, compounds which exhibit $IC_{50}$s as high as 1 mM to 10 mM are considered to possess biological or pharmacological activity.

Alternatively, an in vitro procollagen assay may be used to determine the level of activity and effect of different compounds of the present invention on C-proteinase activity. In the procollagen assay, about 125 ug radiolabeled ($^{14}C$) procollagen is added to 10 units/ml of chicken C-proteinase in a solution of 0.1 M Tris-HCl, 0.1 M NaCl, 0.02% Brij-35, and 5 mM $CaCl_2$ in a total volume of 10 ul. The reaction is allowed to proceed for 15 minutes at 35° C. and is stopped with one-half volume of 3x stop/loading buffer (30 mM EDTA, 30% glycerol, 6% SDS, 0.006% Bromophenolblue). Subsequently, the samples are heated to 100° C. for 4 minutes, and resolved by SDS-PAGE (Novex) using 6% polyacryleamide gels. The protein bands are detected by autoradiography. The amount of enzyme activity is based on the disappearance of the band corresponding to uncleaved procollagen. The $IC_{50}$ of inhibitors can be determined by plotting the percent activity versus inhibitor concentration and estimating the inhibitor concentration which results in 50% activity.

5.4 Indications

Disorders associated with unregulated collagen production or maturation can be treated with the compounds and compositions of the present invention. While not intending to be bound by any particular theory, it is believed that when administered to an animal subject, including a human, the compounds of the invention inhibit C-proteinase in vivo, thereby effectively modulating, regulating or inhibiting collagen production or maturation. As a consequence, the compounds are able to treat or prevent disorders associated with unregulated collagen production or maturation.

Collagen-related disorders which can be treated or prevented according to the invention include pathological fibrosis or scarring, such as endocardial sclerosis, idiopathic interstitial fibrosis, interstitial pulmonary fibrosis, perimuscular fibrosis, Symmers' fibrosis, pericentral fibrosis, hepatitis, dermatofibroma, billary cirrhosis, alcoholic cirrhosis, acute pulmonary fibrosis, idiopathic pulmonary fibrosis, acute respiratory distress syndrome, kidney fibrosis/glomerulonephritis, kidney fibrosis/diabetic nephropathy, scleroderma/systemic, scleroderma/local, keloids, hypertrophic scars, severe joint adhesions/arthritis, myelofibrosis, corneal scarring, cystic fibrosis, muscular dystrophy (duchenne's), cardiac fibrosis, muscular fibrosis/retinal separation, esophageal stricture, payronles disease. Further, fibrotic disorders may be induced or initiated by surgery such as scar revision/plastic surgeries, glaucoma, cataract fibrosis, corneal scarring, joint adhesions, graft vs. host disease, tendon surgery, nerve entrapment, dupuytren's contracture, OB/GYN adhesions/fibrosis, pelvic adhesions, peridural fibrosis, restenosis. Still further fibrotic disorders may be induced by chemotherapy, including, for example lung fibrosis and the like.

5.5 Pharmaceutical Formulations And Routes Of Administration

The compounds described herein, or pharmaceutically acceptable addition salts or hydrates thereof, can be delivered to a subject, including a human, using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. of course, the choice of therapeutic agents that can be co-administered with the compounds of the invention will depend, in part, on the condition being treated.

For example, the compounds of the invention can be administered in cocktails containing agents used to treat the pain and other symptoms and side effects commonly associated with fibrotic disorders. The compounds can also be administered in cocktails containing other agents that are commonly used to treat fibrotic disorders.

The active compound(s) may be administered per se or in the form of a pharmaceutical composition containing the active compound(s) and one or more pharmaceutically acceptable carriers, excipients or diluents. Administered compounds may be enantiomerically pure, or may be mixtures of enantiomers. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations previously described, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

5.5.1 Effective Dosage.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$. as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1.

Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.5.2 Packaging

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of arthritis or any other fibrotic disorder.

6. EXAMPLE

Compound Syntheses

The compounds of the present invention may be synthesized according to known techniques. The following represent preferred methods for synthesizing certain compounds of the invention.

Preparation of Compounds 6.1 through 6.17 (hydroxamation reaction):

To a solution of D,L-2-aminoadipic acid dimethyl ester hydrochloride (0.5 mmol) in $CH_2Cl_2$ (5 mL) was added triethylamine (0.55 mmol), aldehyde (0.55 mmol), and sodium triacetoxyborohydride (0.7 mmol). The reaction mixture was shaken at room temperature for 6 hours, the corresponding isocyanate (0.55 mM) was added and the mixture was shaken for an additional 12 hours, and then quenched with 1 mL of 1 N HCl. The organic phase was washed with water (5 mL), dried over $MgSO_4$, filtered, concentrated and dried. The residue was treated with a freshly prepared hydroxylamine solution (1.5 mL, 1.5 mM) for 12 hours, and then quenched with 2 mL of 1 N HCl, and 6 mL of $CH_2Cl_2$. The organic phase was washed with water (5 mL) , dried over $MgSO_4$, filtered and concentrated. The residue was triturated in ether/hexane (1:1, 5 mL), and dried in vaccuo to leave the compound as a colorless foam.

Preparation of hydroxylamine solution:

A solution of potassium hydroxide (840 mg, 15 mM) in 5 mL of methanol, which became clear upon heating, was poured into a solution of hydroxylamine hydrochloride (690 mg, 10 mM) in 5 mL of methanol, and the resulting mixture was cooled to 0C for 1h.

The $KOH/HONH_2$ solution was filtered, and the fresh filtrate was used for the hydroxamation reaction above.

The following (6.1 thru 6.17) are the spectra of compounds synthesized according to the hydroxamation reaction described above.

6.1 Synthesis of (Compound 102)

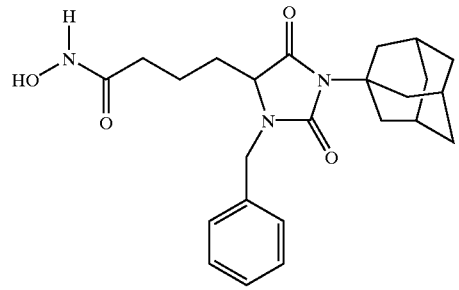

$^1$H NMR (360 MHz, DMSO-d$_6$): 1.23 (m$_c$, 1H, CH$_2$); 1.31 (m, 1H, CH$_2$); 1.66 (m$_c$, 8H), 1.83 (bt, 2H), 2.05 (bs, 3H), 2.33 (bd, 6 H) (Ada-H, CH$_2$); 3.75 (t, J=4 Hz, 1H, CH); 4.20, 4.64 (AA'BB', J~15 Hz, 2H, NCH$_2$); 7.29 (m$_c$, 5H, Ar—H); 8.64, 10.28 (s, ~2H, CONHOH). MS: m/e 426 (M$^+$+1).

6.2 Synthesis of (Compound 174)

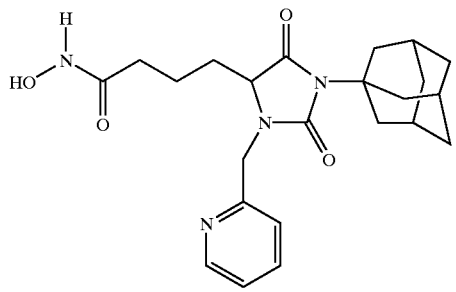

¹H NMR (360 MHz, DMSO-d₆): 1.26 (m$_c$, 1H, CH$_2$); 1.40 (m$_c$, 1H, CH$_2$); 1.65 (m$_c$, 8H), 1.86 (bt, 2H), 2.05 (bs, 3H), 2.33 (bd, 6 H) (Ada-H, CH$_2$); 3.95 (t, J=4 Hz, 1H, CH); 4.31, 4.72 (AA'BB', J=16 Hz, 2H, NCH$_2$); 7.28 (m$_c$, 2H), 7.76 (m$_c$, 1H), 8.49 (d, J=5 Hz, 1H) (Ar—H); 8.62, 10.28 (s, ~2H, CONHOH).

MS: m/e 427 (M$^+$+1).

6.3 Synthesis of (Compound 161)

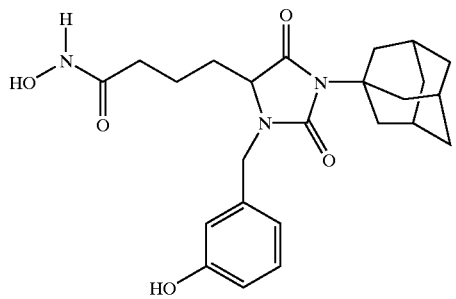

¹H NMR (360 MHz, DMSO-d₆): 1.23 (m$_c$, 1H, CH$_2$); 1.32 (m$_c$, 1H, CH$_2$); 1.67 (m$_c$, 8H), 1.86 (bt, 2H), 2.06 (bs, 3H), 2.34 (bd, 6H) (Ada-H, CH$_2$); 3.71 (t, J=4 Hz, 1H, CH); 4.06, 4.60 (AA'BB', J~14 Hz, 2H, NCH$_2$); 6.65 (m$_c$, 3H), 7.14 (t, J=8 Hz, 1H) (Ar—H); 8.64, 9.39, 10.29 (s, ~3H, CONHOH, OH). MS: m/e 442 (M$^+$+1).

6.4 Synthesis of (Compound 155)

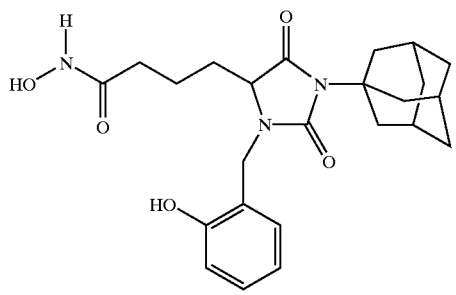

¹H NMR (360 MHz, DMSO-d₆): 1.24 (m$_c$, 1H, CH$_2$); 1.39 (m$_c$, 1H, CH$_2$); 1.64 (m$_c$, 8H), 1.86 (bt, 2H), 2.05 (bs, 3H), 2.33 (bd, 6 H) (Ada-H, CH$_2$); 3.70 (t, J=4 Hz, 1H, CH); 4.10, 4.60 (AA'BB', J~15 Hz, 2H, NCH$_2$); 6.77 (m$_c$, 2H), 7.10 (m$_c$, 2H) (Ar—H); 8.63, 9.58, 10.28 (s, ~3H, CONHOH, OH).

MS: m/e 442 (M$^+$+1).

6.5 Synthesis of (Compound 163)

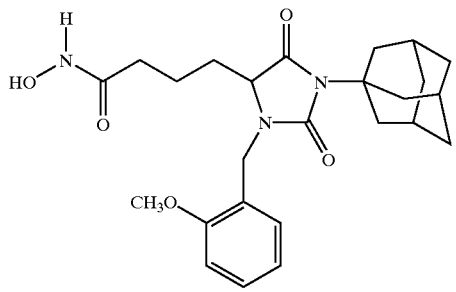

¹H NMR (360 MHz, DMSO-d₆): 1.26 (m$_c$, 1H, CH$_2$); 1.39 (m$_c$, 1H, CH$_2$); 1.65 (m$_c$, 8H), 1.88 (bt, 2H), 2.06 (bs, 3H), 2.34 (bd, 6H) (Ada-H, CH$_2$); 3.68 (t, J=4 Hz, 1H, CH); 3.79 (s, 3H, CH$_3$); 4.16, 4.62 (AA'BB', J~15 Hz, 2H, NCH$_2$); 6.92 (m$_c$, 1H), 7.00 (d, 1H), 7.18 (dd, 1H), 7.28 (m$_c$, 1H) (Ar—H); 8.64, 10.30 (s, ~2H, CONHOH).

MS: m/e 456 (M$^+$+1).

6.6 Synthesis of (Compound 139)

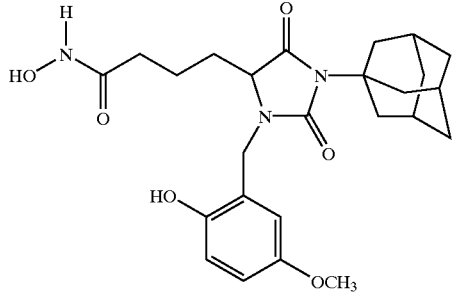

¹H NMR (360 MHz, DMSO-d₆): 1.24 (m$_c$, 1H, CH$_2$); 1.38 (m$_c$, 1H, CH$_2$); 1.64 (m$_c$, 8H), 1.87 (bt, 2H), 2.05 (bs, 3H), 2.33 (bd, 6H) (Ada-H, CH$_2$); 3.63 (s, 3H, CH$_3$); 3.71 (t, J~4 Hz, 1H, CH); 4.10, 4.55 (AA'BB', J~15 Hz, 2H, NCH$_2$); 6.68 (m$_c$, 3H, Ar—H); 8.64, 9.11, 10.29 (s, ~3H, CONHOH, OH).

MS: m/e 472 (M$^+$+1).

6.7 Synthesis of (Compound 137)

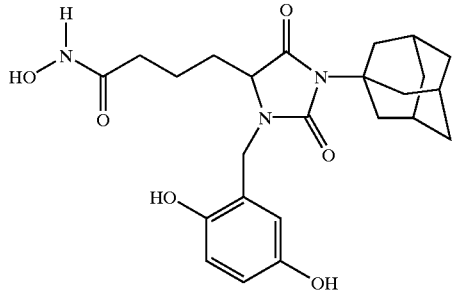

¹H NMR (360 MHz, DMSO-d₆): 1.23 (m$_c$, 1H, CH$_2$); 1.38 (m$_c$, 1H, CH$_2$); 1.64 (m$_c$, 8H), 1.88 (bt, 2H), 2.05 (bs, 3H), 2.33 (bd, 6H) (Ada-H, CH$_2$); 3.70 (t, J~4 Hz, 1H, CH); 4.04, 4.50 (AA'BB', J~15 Hz, 2H, NCH$_2$); 6.48, 6.62 (m$_c$, 3H, Ar—H); 8.66, 8.84, 10.29 (s, ~4H, CONHOH, OH).

MS: m/e 458 (M$^+$+1).

6.8 Synthesis of (Compound 168)

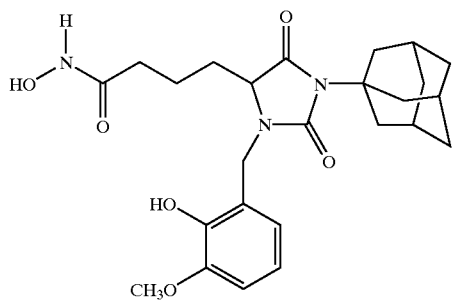

¹H NMR (360 MHz, DMSO-d$_6$): 1.20 (m$_c$, 1H, CH$_2$); 1.38 (m$_c$, 1H, H$_2$); 1.65 (m$_c$, 8H), 1.88 (bt, 2H), 2.06 (bs, 3H), 2.33 (bd, 6 H) (Ada-H, CH$_2$); 3.69 (t, J~4 Hz, 1H, CH); 3.78 (s, 3H, CH$_3$); 4.15, 4.61 (AA'BB', J~15 Hz, 2H, NCH$_2$); 6.73, 6.90 (m$_c$, 3H, Ar—H); 8.64, 8.77, 10.29 (s, ~3H, CONHOH, OH).

MS: m/e 472 (M$^+$+1).

6.9 Synthesis of (Compound 179)

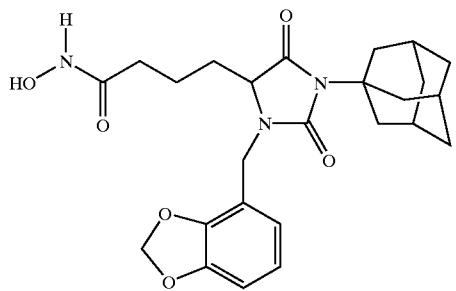

¹H NMR (360 MHz, DMSO-d$_6$): 1.23 (m$_c$, 1H, CH$_2$); 1.37 (m$_c$, 1H, CH$_2$); 1.64 (m$_c$, 8H), 1.85 (bt, 2H), 2.05 (bs, 3H), 2.32 (bd, 6 H) (Ada-H, CH$_2$); 3.77 (t, J~4 Hz, 1H, CH); 4.15, 4.61 (AA'BB', J~15 Hz, 2H, NCH$_2$); 6.00 (s, 2H, OCH$_2$); 6.78 (m$_c$, 3H, Ar—H); 8.63, 10.29 (s, ~2H, CONHOH).

MS: m/e 470 (M$^+$+1).

6.10 Synthesis of (Compound 131)

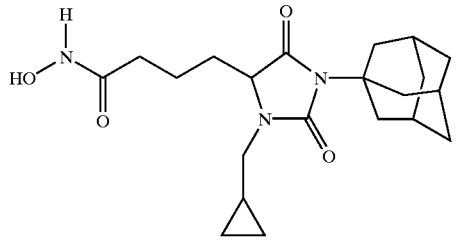

¹H NMR (360 MHz, DMSO-d$_6$): 0.23, 0.47 (m$_c$, 4H, CH$_2$); 0.94, 1.25, 1.45 (m$_c$, 3H), 1.79 (m$_c$, 8H), 1.92 (t, 2H), 1.96 (bs, 3H), 3.33 (bd, 6H) (Ada-H, CH, CH$_2$); 2.88, 3.27 (dd, J=7 Hz and 14 Hz, 2H, CH$_2$); 4.03 (t, J=4 Hz, 1H, CH); 8.64, 10.31 (s,2H, CONHOH). MS: m/e 390 (M$^+$+1).

6.11 Synthesis of (Compound 127)

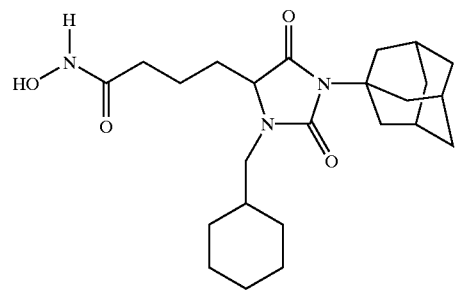

¹H NMR (360 MHz, DMSO-d$_6$): 0.86, 1.22, 1.63 (m$_c$, 21H); 1.92 (t, 2H), 2.03 (bs, 3H), 2.30 (bd, 6H) (Ada-H, CH, CH$_2$); 2.78, 3.26 (bdd, 2H, NCH$_2$); 3.93 (t, J=4 Hz, 1H, CH); 8.65, 10.31 (s, ~2H, CONHOH). MS: m/e 432 (M$^+$+1).

6.12 Synthesis of (Compound 128)

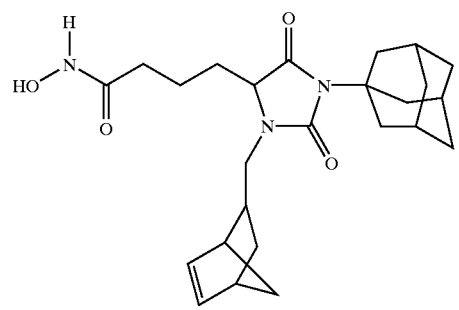

¹H NMR (360 MHz, DMSO-d$_6$): 1.30, 1.69 (m$_c$, 13H); 1.94 (bt, 2H), 2.06 (bs, 3H), 2.31 (m$_c$, 6H), 2.70 (m$_c$, 3H), 3.11 (m$_c$, 1H) (Ada-H, CH, CH$_2$); 3.98, 4.03 (t, J~4Hz, 1H, CH); 6.03, 6.19 (m$_c$, 2H, =CH); 8.64, 10.31 (s, ~2H, CONHOH) MS: m/e 442 (M$^+$+1).

6.13 Synthesis of (Compound 192)

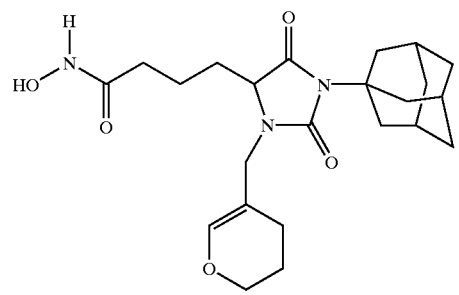

¹H NMR (360 MHz, DMSO-d$_6$): 1.26, 1.36 (m$_c$, 2H, CH$_2$); 1.64, 1.76 36 (m$_c$, 12H), 1.92 (bt, 2H), 2.04 (bs, 3H), 2.31 (bd, 6H) (Ada-H, CH, CH$_2$); 3.40 (d, J=14 Hz, 1H), 3.76 (t, J~4 Hz, 1H), 3.83 (bt, J~4 Hz, 2H), 4.00 (d, J~14 Hz, 1H) (NCH$_2$, OCH$_2$, CH); 6.46 (s, 1H, =CH); 8.63, 10.31 (s, ~2H, CONHOH).

MS: m/e 432 (M$^+$+1).

6.14 Synthesis of (Compound 176)

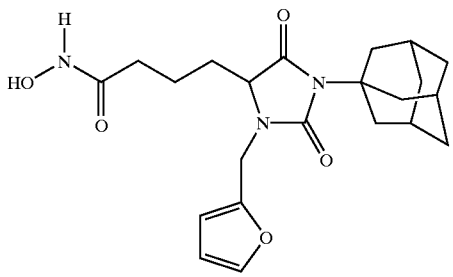

¹H NMR (360 MHz, DMSO-d₆): 1.25 (m_c, 2H, CH₂); 1.64 (m_c, 8H), 1.86 (bt, 2H), 2.05 (bs, 3H), 2.32 (bd, 6 H) (Ada-H, CH₂); 3.77 (t, J=4 Hz, 1H, CH); 4.30, 4.56 (AA'BB', J~16 Hz, 2H, NCH₂); 6.39, 7.59 (m_c, 3H, =CH); 8.63, 10.29 (s, ~2H, CONHOH).
MS: m/e 416 (M⁺+1).

6.15 Synthesis of (Compound 107)

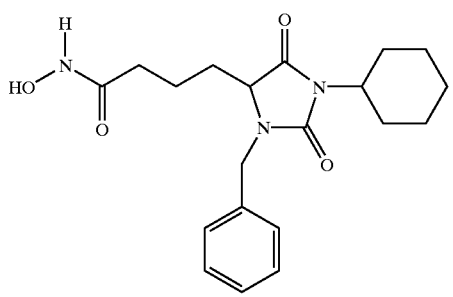

¹H NMR (360 MHz, DMSO-d₆): 1.29 (m_c, 5H), 1.68 (m_c, 9H), 2.01 (m_c, 2H) (H₂); 3.78 (m_c, 1H, NCH); 3.89 (t, J~4 Hz, 1H, CH); 4.25, 4.68 (AA'BB', J~15 Hz, 2H, NCH₂); 7.29 (m_c, 5H, Ar—H); 8.62, 10.27 (s, ~2H, CONHOH).
MS: m/e 374 (M⁺+1).

6.16 Synthesis of (Compound 195)

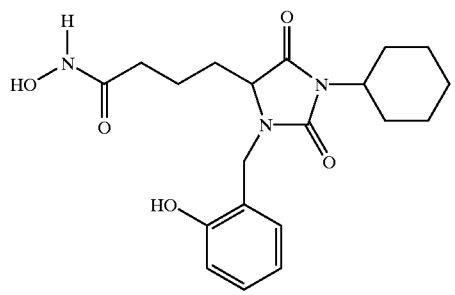

¹H NMR (360 MHz, DMSO-d₆): 1.28 (m_c, 5H), 1.58, 1.72, 1.87 (m_c, 9H), 2.01 (m_c, 2H) (CH₂); 3.79 (m_c, 2H, NCH, CH); 4.18, 4.64 (AA'BB', J~15 Hz, 2H, NCH₂); 6.78, 7.11 (m_c, 4H, Ar—H); 8.63, 9.60, 10.29 (s, ~3H, CONHOH, OH).
MS: m/e 390 (M⁺+1).

6.17 Synthesis of (Compound 198)

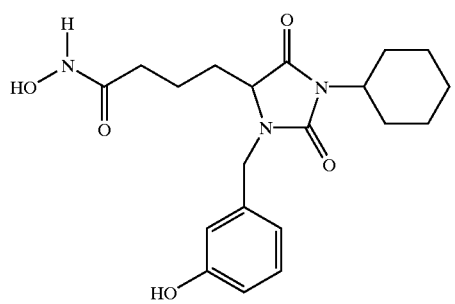

¹H NMR (360 MHz, DMSO-d₆): 1.25 (m_c, 5H), 1.72 (m_c, 9H), 2.05 (m_c, 2H) (CH₂); 3.79 (m_c, 1H, NCH); 3.86 (t, J~4 Hz, 1H, CH); 4.13, 4.64 (AA'BB', J~15 Hz, 2H, NCH₂); 6.68 (m_c, 3H), 7.13 (t, J~8 Hz, 1H) (Ar—H); 8.62, 9.38, 10.28 (s, ~3H, CONHOH, OH).
MS: m/e 390 (M⁺+1).

6.18 Synthesis of (Compound 199)

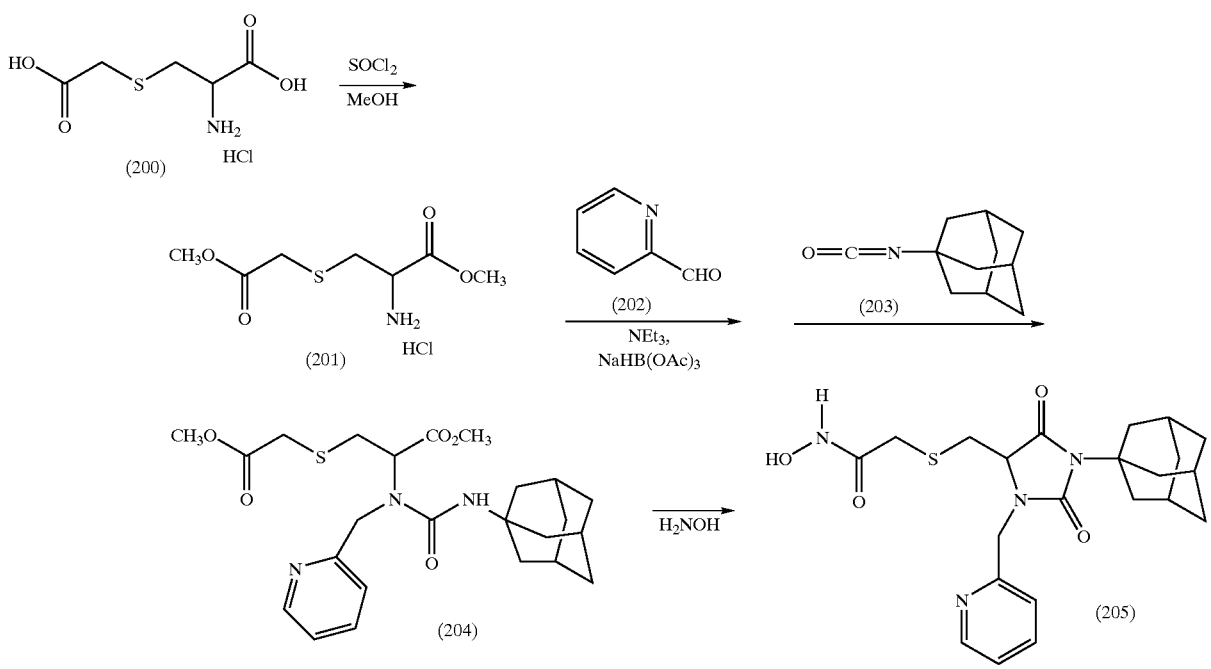

Compound 200 is commercially available (Aldrich). Compound 200 was mixed with SOCl$_2$ in MeOH to yield compound 201. To compound 201 (0.5 mM) in CH$_2$Cl$_2$ (5 mL) was added triethylamine (0.55 mM), aldehyde 202 (0.55 mM), and sodium triacetoxyborohydride (0.7 mM). The reaction mixture was shaken at room temperature for six hours, and then adamantyl isocynate 203 (0.55 mM) was added. The mixture was shaken for an additional twelve hours and then quenched with 1 mL of 1 N HCl. The organic phase was washed with water (5 mL), dried over MgSO$_1$, filtered, and concentrated to yield residue 204. Residue 204 was treated with freshly prepared hydroxylamine solution (1.5 mL, 1.5 mM) for twelve hours, and then quenched with 2 mL of 1N HCl, and 6 ml of CH$_2$Cl$_2$. The organic phase was washed with water (5 mL), dried over MgSO$_4$, filtered and concentrated to yield title compound 205. Title compound 205 is triturated in ether/hexane (1.1, 5 mL), and dried in vaccuo.

6.19 Synthesis of (Compound 200)

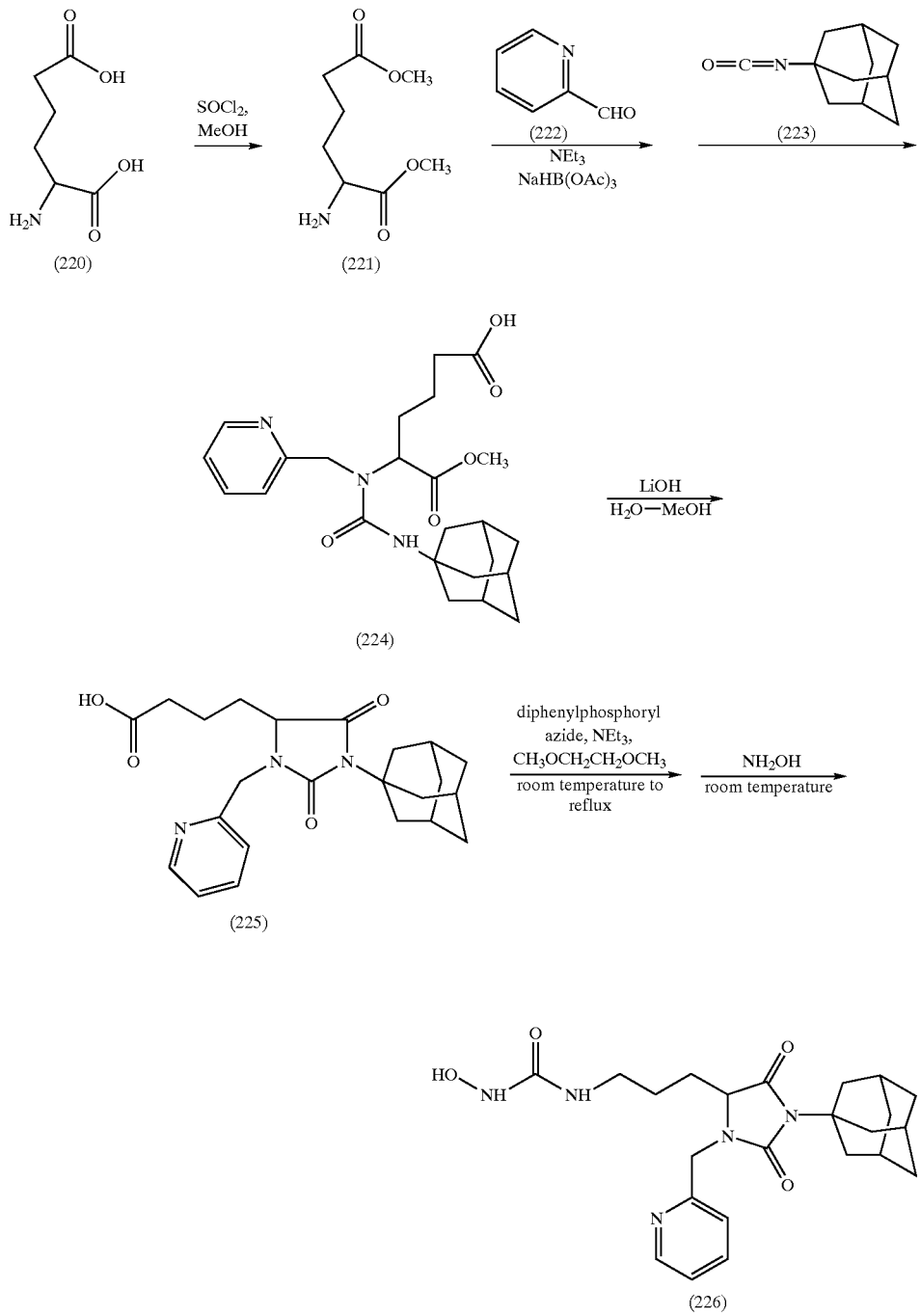

D,L-2-amino-butanedioic acid 220 was mixed with SOCl$_2$ in MeOH to yield D,L-2-amino-butanedioic acid 221. To compound 221 (0.5 mM) in CH$_2$Cl$_2$ (5 mL) was added triethylamine (0.55 mM), aldehyde 222 (0.55 mM), and sodium triacetoxyborohydride (0.7 mM). The reaction mixture was shaken at room temperature for six hours, and then admantylisocynate 223 (0.55 mM) was added. The mixture was shaken for an additional twelve hours and then quenched with 1 mL of 1 N HCl. The organic phase was washed with water (5 mL), dried over MgSO$_4$, filtered, and concentrated to yield residue 224. Residue 224 was treated with LiOH to yield hydantoin 225. Hydantoin 225 was mixed with diphenylphosphoryl azide, triethylamine, and ethylene glycol and refluxed at room temperature to form an isocyanate. The isocyanate was treated with freshly prepared hydroxylamine solution (1.5 mL, 1.5 mM) for twelve hours, and then quenched with 2 mL of 1N HCl, and 6 mL of CH$_2$Cl$_2$. The organic phase was washed with water (5 mL), dried over MgSO$_4$, filtered and concentrated to yield title compound 226.

6.20 Synthesis of Other Compounds

Other compounds of the invention can be synthesized by routine modification of the above-described syntheses, or by other methods that are well-known in the art. Appropriate starting materials are commercially available or can by synthesized using routine methods.

7. EXAMPLE

C-Proteinase IC$_{50}$ Assays

The following assay may be used to determine the level of activity and effect of the different compounds of the present invention on C-proteinase activity.

To determine inhibition of recombinant human C-proteinase, 60 μl of a reaction mix (final concentration in 100 μl of 0.05M Tris-HCl pH 7.6, 0.1M NaCl, 0.02% Brij-35, 5 mM CaCl$_2$ and 50 μM of a fluorogenic peptide) was added to 20 μl of the inhibitor in a 96 well plate. The reaction was started with the addition of 20 μl of the recombinant human C-proteinase mix. The reaction proceeded for 4 hours at 37° C. and the fluorescence was measured using a Bio-Tek Fl-600. The IC$_{50}$ was determined by plotting the percentage of activity versus the inhibitor concentration and estimating the inhibitor concentration that gives 50% activity of the control The IC$_{50}$ values of exemplary inhibitors of the present invention are shown in Table 10.

TABLE 10

C-Proteinase Inhibitor IC$_{50}$ (μM) Values

| Compound # | IC$_{50}$ (μM) |
|---|---|
| 102 | 0.77 |
| 174 | 0.21 |
| 161 | 0.14 |
| 155 | 0.27 |
| 163 | 0.60 |
| 139 | 0.26 |
| 137 | 0.059 |
| 168 | 0.43 |
| 179 | 0.23 |
| 131 | 0.43 |
| 127 | 0.29 |
| 128 | 0.40 |
| 192 | 0.21 |

TABLE 10-continued

C-Proteinase Inhibitor IC$_{50}$ (μM) Values

| Compound # | IC$_{50}$ (μM) |
|---|---|
| 176 | 0.23 |
| 107 | 3.33 |
| 195 | 1.08 |
| 198 | 1.24 |
| 193 | 22.93 |
| 194 | 18.99 |
| 199 | 0.29 |

7.2 Tissue Culture Assay for the Determination of C-proteinase Activity and the IC$_{50}$ of Inhibitors C-proteinase activity and the IC$_{50}$ of inhibitors in vivo may be determined in tissue culture assays by measuring the production of procollagen and mature collagen in conditioned medium before and after treatment with a particular compound. The ratio of collagen and procollagen will directly correlate to the cellular conversion of the precursor to the mature collagen product, and as such indicate the C-proteinase activity.

Alternatively, the media content of C-propeptide/cell may be determined, and compared for untreated cells and inhibitor-treated cells.

7.3 Animal Models for the Determination of C-proteinase Activity and the Efficacy of Inhibitors Several animal models which mimic clinical disorders related to unregulated or inappropriate collagen production are known in the art and may be employed to determine the in vivo efficacy of the compounds of the invention. These animal models include a wound chamber model in rats (Schilling et al., 1959, Surgery 46:702–710), an estradiol stimulated uterus expansion model (Mandell et al., 1982, The Journal of Biological Chemistry 257:5268–5273), and an induced angiogenesis model (Matrigel) (Passaniti et al., 1992, Laboratory Investigation 67:519–528). Further animal models include clinical disorder models like liver fibrosis models (Tsukamoto et al., 1990, Seminar in Liver Disease 10:56–65; Kock-Weser, 1952, Laboratory Investigation 1:324–331; Marrione, 1949, American Journal of Pathology 25:273–285; Tams, 1957, American Journal of Pathology 33:13–27; Wahl et al., 1986, Journal of Experimental Medicine 163:884–902), a pulmonary fibrosis model (Kelly et al., 1980, Journal of Laboratory Clinical Medicine 96:954–964), arterial restenosis models (Jackson, 1994, Trends of Cardiovascular Medicine 4:122–130; Clowes et al., 1983, Laboratory Investigation 49:327–333), a kidney fibrosis model (Yamamoto et al., 1987, Kidney International 32:514–525), a tendon repairing model (Franklin et al., 1986, The Journal of Laboratory and Clinical Medicine 108:103–108), a tumor growth model (Kiohs, et al., 1985, JNCL 75:353–359), a trabeculectomy model (Lahery et al., 1989, Journal of Ocular Pharmacology 5:155–179), and an abdominal adhesions model (Williams et al., 1992, Journal of Surgical Research 52:65–70).

8.0 CONCLUSION

The present invention is not to be limited in scope by the exemplified embodiments which are intended as illustrations of single aspects of the invention, and any compounds and methods for the use thereof which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A compound having the structural formula:

(Ia)

(Ia')

or pharmaceutically acceptable salts thereof, wherein:
- m is an integer from 0 to 3 when X is $NR_{19}$ or an integer from 1 to 3 when X is S or O;
- p is an integer from 1 to 4 when X is $NRg9$ or an integer from 1 to 3 when X is S or O;
- n is an integer from 1 to 3;
- X is $NR_{19}$, S, or O;
- $R_{19}$ is selected from the group consisting of hydrogen, ($C_1$–$C_5$) alkyl, and ($C_1$–$C_5$) substituted alkyl;
- $R_1$ and $R_2$ are each independently selected from the group consisting of ($C_1$–$C_{10}$) alkyl, ($C_1$–$C_{10}$) substituted alkyl, ($C_3$–$C_{10}$) alkenyl, ($C_3$–$C_{10}$) substituted alkenyl, ($C_3$–$C_{10}$) alkynyl, ($C_3$–$C_{10}$) substituted alkynyl, ($C_3$–$C_{20}$) cycloalkyl, ($C_3$–$C_{20}$) substituted cycloalkyl, ($C_5$–$C_{20}$) aryl, ($C_5$–$C_{20}$) aryl independently substituted with one or more $Y^1$, alkaryl, and alkaryl independently substituted with one or more $Y^1$;
- $R_{20}$ and $R_{21}$ are each independently selected from the group consisting of hydrogen, ($C_1$–$C_{10}$) alkyl, and ($C_6$–$C_{26}$) alkaryl; and
- each $Y^1$ is independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, and —OCF$_3$; wherein each R is independently selected from the group consisting of hydrogen, ($C_1$–$C_8$) alkyl, ($C_3$–$C_8$) alkenyl, ($C_5$–$C_{20}$) aryl, and ($C_6$–$C_{26}$) alkaryl;
- with the proviso that the sum of m and p is 1, 2, 3 or 4.

2. The compound of claim 1 having the structural formula:

or pharmaceutically acceptable salts thereof, wherein:
- a is an integer from 2 to 5; and
- $R_1$, $R_2$, and $R_{20}$ are as defined in claim 1.

3. The compound of claim 2 having the structural formula:

or pharmaceutically acceptable salts thereof, wherein:
- a, $R_1$, and $R_{20}$ are as defined in claim 2; and
- $R_3$, $R_4$, $R_5$, $R_6$, and $R_7$ are each independently selected from the group consisting of, -hydrogen, -halogen, -trihalomethyl, —R, —C(O)OR, —CN, —C(O)—NR—OR, —C(NRR)=N—OR, —C(O)—R, —C(O) NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, and —OCF$_3$; where each R is independently selected from the group consisting of —H, ($C_1$–$C_8$) alkyl, ($C_3$–$C_8$) alkenyl, ($C_3$–$C_8$) alkynyl, ($C_5$–$C_{20}$) aryl, and ($C_6$–$C_{26}$) alkaryl.

4. The compound of claim 3 having the structural formula:

or pharmaceutically acceptable salts thereof, wherein $R_1$ is as defined in claim 3.

5. The compound of claim 4 selected from the group consisting of 4-(3-Benzyl-1-naphthalen-1-yl-2,5-dioxo-imidazolidin-4-yl)-N-hydroxy-butyramide, 4-(1-Adamantan-1-yl-3-benzyl-2,5-dioxo-imidazolidin-4-yl)-N- hydroxy-butyramide, 4-(3-Benzyl-2,5-dioxo-1-propyl-imidazolidin-4-yl)-N-hydroxy-butyramide, 4-(3-Benzyl-1-ethyl-2,5-dioxo-imidazolidin-4-yl)-N-hydroxy-butyramide, 4-(3-Benzyl-1-hexyl-2,5-dioxo-imidazolidin-4-yl)-N-hydroxy-butyramide, 4-1,3-Dibenzyl-2,5-dioxo-imidazolidin-4-yl)-N-hydroxy-butyramide, 4-(3-Benzyl-1-cyclohexyl-2,5-dioxo-imidazolidin-4-yl)-N-hydroxy-butyramide, and 4-[3-Benzyl-2,5-dioxo-1-1,1,3,3-tetramethyl-butyl)-imidazolidin-4-yl]-N-hydroxy-butyramide.

6. The compound of claim 2 having the structural formula:

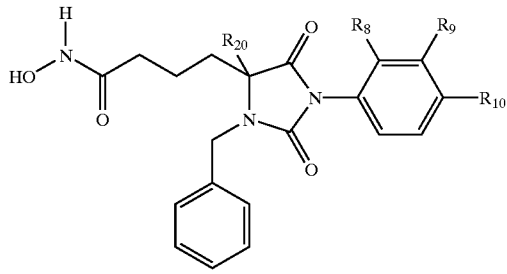

or pharmaceutically acceptable salts thereof, wherein:
$R_8$, $R_9$ and $R_{10}$ are each independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, and —OCF$_3$; where each R is independently selected from the group consisting of —H, ($C_1$–$C_8$) alkyl, ($C_3$–$C_8$) alkenyl, ($C_3$–$C_8$) alkynyl, ($C_5$–$C_{20}$) aryl, and ($C_6$–$C_{26}$) alkaryl; and
$R_{20}$ is as defined in claim 2.

7. The compound of claim 6 selected from the group consisting of 4-(3-Benzyl-2,5-dioxo-1-phenyl-imidazolidin-4-yl)-N-hydroxy-butyramide, 4-[3-Benzyl-1-(4-methoxy-phenyl)-2,5-dioxo-imidazolidin-4-yl]-N-hydroxy-butyramide, 4-[3-Benzyl-1-(2,4-dimethoxy-phenyl)-2,5-dioxo-imidazolidin-4-yl]-N-hydroxy-butyramide, 4-[3-Benzyl-1-(4-nitro-phenyl)-2,5-dioxo-imidazolidin-4-yl]-N-hydroxy-butyramide, 4-(3-Benzyl-1-biphenyl-2-yl-2,5-dioxo-imidazolidin-4-yl)-N-hydroxy-butyramide, 4-[3-Benzyl-1-(4-chloro-phenyl)-2,5-dioxo-imidazolidin-4-yl]-N-hydroxy-butyramide, 4-[3-Benzyl-1-(3-cyano-phenyl)-2,5-dioxo-imidazolidin-4-yl]-N-hydroxy-butyramide, 4-[3-Benzyl-1-(3-chloro-phenyl)-2,5-dioxo-imidazolidin-4-yl]-N-hydroxy-butyramide, 4-(3-Benzyl-2,5-dioxo-1-p-tolyl-imidazolidin-4-yl)-N-hydroxy-butyramide, 4-[3-Benzyl-1-(3-methoxymethyl-phenyl)-2,5-dioxo-imidazolidin-4-yl]-N-hydroxy-butyramide, 4-[3-Benzyl-1-(2,4-difluoro-phenyl)-2,5-dioxo-imidazolidin-4-yl]-N-hydroxy-butyramide, 4-[3-Benzyl-1-(2,4-dichloro-phenyl)-2,5-dioxo-imidazolidin-4-yl]-N-hydroxy-butyramide, 4-[3-Benzyl-1-(4-t-butyl-phenyl)-2,5-dioxo-imidazolidin-4-yl]-N-hydroxy-butyramide, 4-[3-Benzyl-2,5-dioxo-1-(4-phenoxy-phenyl)-imidazolidin-4-yl]-N-hydroxy-butyramide, 4-[3-Benzyl-1-(4-t-butoxy-phenyl)-2,5-dioxo-imidazolidin-4-yl]-N-hydroxy-butyramide, and 4-[3-Benzyl-1-(2,3-dimethyl-phenyl)-2,5-dioxo-imidazolidin-4-yl]-N-hydroxy-butyramide.

8. The compound of claim 2 having the structural formula:

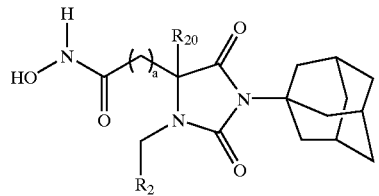

or pharmaceutically acceptable salts thereof, wherein a, $R_2$, and $R_{20}$ are as defined in claim 2.

9. The compound of claim 8 having the structural formula:

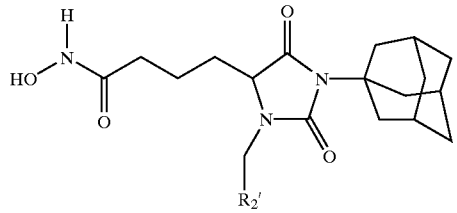

or pharmaceutically acceptable salts thereof, wherein $R_2'$ is selected from the group consisting of ($C_1$–$C_{10}$) alkyl, ($C_1$–$C_{10}$) substituted alkyl, ($C_3$–$C_{10}$) alkenyl, ($C_3$–$C_{10}$) substituted alkenyl, ($C_3$–$C_{10}$) alkynyl, ($C_3$–$C_{10}$) substituted alkynyl, ($C_3$–$C_{20}$) cycloalkyl, ($C_3$–$C_{20}$) substituted cycloalkyl, ($C_5$–$C_{20}$) aryl, ($C_5$–$C_{20}$) aryl independently substituted with one or more $Y^1$, alkaryl, alkaryl independently substituted with one or more $Y^1$; and $Y^1$ are as defined in claim 2.

10. The compound of claim 9 selected from the group consisting of 4-(1-Adamantan-1-yl-3-cyclohex-3-enylmethyl-2,5-dioxo-imidazolidin-4-yl)-N-hydroxy-butyramide, 4-(1-Adamantan-1-yl-3-cyclohexylmethyl-2,5-dioxo-imidazolidin-4-yl)-N-hydroxy-butyramide, 4-(1-Adamantan-1-yl-3-bicyclo[2.2.1]hept-5-en-2-ylmethyl-2,5-dioxo-imidazolidin-4-yl)-N-hydroxy-butyramide, 4-[1-Adamantan-1-yl-3-(3-methyl-butyl)-2,5-dioxo-imidazolidin-4-yl]-N-hydroxy-butyramide, 4-(1-Adamantan-1-yl-2,5-dioxo-3-phenethyl-imidazolidin-4-yl)-N-hydroxy-butyramide, 4-(1-Adamantan-1-yl-3-cyclopropylmethyl-2,5-dioxo-imidazolidin-4-yl)-N-hydroxy-butyramide, 4-[1-Adamantan-1-yl-3-(2,2-dimethyl-propyl)-2,5-dioxo-imidazolidin-4-yl]-N-hydroxy-butyramide, 4-(1-Adamantan-1-yl-3-naphthalen-2-ylmethyl-2,5-dioxo-imidazolidin-4-yl)-N-hydroxy-butyramide, and 4-[1-Adamantan-1-yl-3-(2-cyclohexyl-ethyl)-2,5-dioxo-imidazolidin-4-yl]-N-hydroxy-butyramide; compound with ethane.

11. The compound of claim 8 having the structural formula:

51

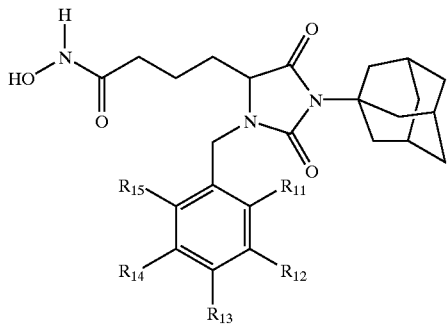

or pharmaceutically acceptable salts thereof, wherein:

$R_{11}$, $R_{12}$, $R_{13}$, $R_{14}$, and $R_{15}$ is each independently selected from the group consisting of -halogen, -trihalomethyl, —R, —C(O)OR, —CN, —C(O)—NR—OR, —C(NRR)=N—OR, —C(O)—R, —C(O)NRR, —C(S)NRR, —C(NRR)=NR, —NRR, —NO$_2$, —N$_3$, —NR—C(O)R, —NR—C(O)—NRR, —NR—C(O)—OR, —NR—SO$_2$—R, —NR—C(S)—NRR, —NR—C(O)R, —NR—C(O)—NRR, —NR—C(S)—NRR, —OR, —P(O)(OH)(NRR), —P(O)(OH)$_2$, —SO$_2$R, —S(O)—R, —SO$_3$H, —SR, —SO$_2$—NRR, and —OCF$_3$; where each R is independently selected from the group consisting of —H, ($C_1$–$C_8$) alkyl, ($C_3$–$C_8$) alkenyl, ($C_5$–$C_{20}$) aryl, and ($C_6$–$C_{26}$) alkaryl.

12. The compound of claim 11 selected from the group consisting of 4-[1-Adamantan-1-yl-3-(3,5-dimethoxy-benzyl)-2,5-dioxo-imidazolidin-4-yl]-N-hydroxy-butyramide, 4-[1-Adamantan-1-yl-3-(3,5-dichloro-benzyl)-2,5-dioxo-imidazolidin-4-yl]-N-hydroxy-butyramide, 4-[1-Adamantan-1-yl-3-(2,5-dihydroxy-benzyl)-2,5-dioxo-imidazolidin-4-yl]-N-hydroxy-butyramide, 4-[1-Adamantan-1-yl-3-(2-hydroxy-4-methoxy-benzyl)-2,5-dioxo-imidazolidin-4-yl]-N-hydroxy-butyramide, 4-[1-Adamantan-1-yl-3-(2-hydroxy-4-methoxy-benzyl)-2,5-dioxo-imidazolidin-4-yl]-N-hydroxy-butyramide, 4-[1-Adamantan-1-yl-3-(5-chloro-2-hydroxy-benzyl)-2,5-dioxo-imidazolidin-4-yl]-N-hydroxy-butyramide, 4-[1-Adamantan-1-yl-3-(2-hydroxy-5-trifluoromethoxy-benzyl)-2,5-dioxo-imidazolidin-4-yl]-N-hydroxy-butyramide, 4-[1-Adamantan-1-yl-3-(2-hydroxy-5-nitro-benzyl)-2,5-dioxo-imidazolidin-4-yl]-N-hydroxy-butyramide, 4-[1-Adamantan-1-yl-3-(2-hydroxy-6-methoxy-benzyl)-2,5-dioxo-imidazolidin-4-yl]-N-hydroxy-butyramide, 4-[1-Adamantan-1-yl-3-(2,6-dimethoxy-benzyl)-2,5-dioxo-imidazolidin-4-yl]-N-hydroxy-butyramide, 4-[1-Adamantan-1-yl-3-(3,5-dihydroxy-benzyl)-2,5-dioxo-imidazolidin-4-yl]-N-hydroxy-butyramide, and 4-[1-Adamantan-1-yl-3-(5-bromo-2-hydroxy-3-methoxy-benzyl)-2,5-dioxo-imidazolidin-4-yl]-N-hydroxy-butyramide.

13. The compound of claim 11 having the structural formula:

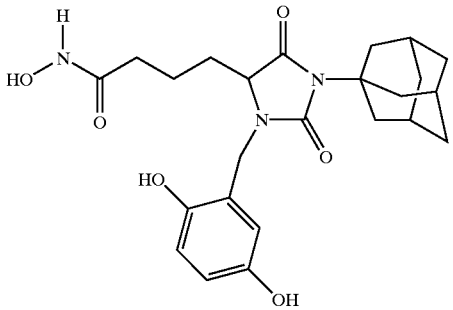

14. The compound of claim 8 having the structural formula:

52

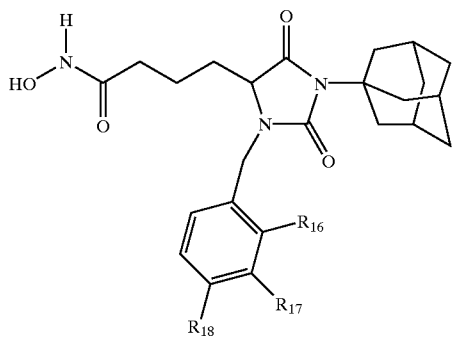

or pharmaceutically acceptable salts thereof, wherein $R_{14}$ and $R_{15}$ are hydrogen.

15. The compound of claim 14 selected from the group consisting of 4-(1-Adamantan-1-yl-3-benzyl-2,5-dioxo-imidazolidin-4-yl)-N-hydroxy-butyramide, 4-[1-Adamantan-1-yl-3-(4-chloro-benzyl)-2,5-dioxo-imidazolidin-4-yl]-N-hydroxy-butyramide, 4-[1-Adamantan-1-yl-3-(4-methoxy-benzyl)-2,5-dioxo-imidazolidin-4-yl]-N-hydroxy-butyramide, 4-(1-Adamantan-1-yl-3-biphenyl4-ylmethyl-2,5-dioxo-imidazolidin-4-yl)-N-hydroxy-butyramide, 4-[1-Adamantan-1-yl-3-(4-dimethylamino-benzyl)-2,5-dioxo-imidazolidin-4-yl]-N-hydroxy-butyramide, 4-[1-Adamantan-1-yl-3-(4-nitro-benzyl)-2,5-dioxo-imidazolidin-4-yl]-N-hydroxy-butyramide, 4-[1-Adamantan-1-yl-2,5-dioxo-3-(4-phenoxy-benzyl)-imidazolidin-4-yl]-N-hydroxy-butyramide, 4-[1-Adamantan-1-yl-3-(4-fluoro-benzyl)-2,5-dioxo-imidazolidin-4-yl]-N-hydroxy-butyramide, 4-[1-Adamantan-1-yl-3-(2-hydroxy-benzyl)-2,5-dioxo-imidazolidin-4-yl]-N-hydroxy-butyramide, 4-[1-Adamantan-1-yl-2,5-dioxo-3-(4-trifluoromethyl-benzyl)-imidazolidin-4-yl]-N-hydroxy-butyramide, 4-[1-Adamantan-1-yl-3-(4-hydroxy-benzyl)-2,5-dioxo-imidazolidin-4-yl]-N-hydroxy-butyramide, 4-[1-Adamantan-1-yl-3-(4-methyl-benzyl)-2,5-dioxo-imidazolidin-4-yl]-N-hydroxy-butyramide, 4-[1-Adamantan-1-yl-3-(3,4-dimethoxy-benzyl)-2,5-dioxo-imidazolidin-4-yl]-N-hydroxy-butyramide, 4-[1-Adamantan-1-yl-3-(2,4-difluoro-benzyl)-2,5-dioxo-imidazolidin-4-yl]-N-hydroxy-butyramide, 4-[1-Adamantan-1-yl-3-(3-hydroxy-benzyl)-2,5-dioxo-imidazolidin-4-yl]-N-hydroxy-butyramide, 4-[1-Adamantan-1-yl-3-(2,3-dimethoxy-benzyl)-2,5-dioxo-imidazolidin-4-yl]-N-hydroxy-butyramide, 4-[1-Adamantan-1-yl-3-(2-methoxy-benzyl)-2,5-dioxo-imidazolidin-4-yl]-N-hydroxy-butyramide, 4-[1-Adamantan-1-yl-3-(2,4-dihydroxy-benzyl)-2,5-dioxo-imidazolidin-4-yl]-N-hydroxy-butyramide, 4-[1-Adamantan-1-yl-3-(2-nitro-benzyl)-2,5-dioxo-imidazolidin-4-yl]-N-hydroxy-butyramide, 4-[1-Adamantan-1-yl-3-(3-hydroxy4-methoxy-benzyl)-2,5-dioxo-imidazolidin-4-yl]-N-hydroxy-butyramide, 4-[1-Adamantan-1-yl-3-(2,3-dihydroxy-benzyl)-2,5-dioxo-imidazolidin-4-yl]-N-hydroxy-butyramide, 4-[1-Adamantan-1-yl-3-(2-hydroxy-3-methoxy-benzyl)-2,5-dioxo-imidazolidin-4-yl]-N-hydroxy-butyramide, 2-[3-Adamantan-1-yl-5-(3-hydroxycarbamoyl-propyl)-2,4-dioxo-imidazolidin-1-ylmethyl]-benzoic acid, 4-[1-Adamantan-1-yl-3-(3-methyl-benzyl)-2,5-dioxo-imidazolidin-4-yl]-N-hydroxy-butyramide, 4-[1-Adamantan-1-yl-3-(3-methoxy-benzyl)-2,5-dioxo-imidazolidin-4-yl]-N-hydroxy-butyramide, 4-[1-Adamantan-1-yl-3-(3-chloro-benzyl)-2,5-dioxo-imidazolidin-4-yl]-N-hydroxy-butyramide, and 3-[3-Adamantan-1-yl-5-(3-hydroxycarbamoyl-propyl)-2,4-dioxo-imidazolidin-1-ylmethyl]-benzoic acid.

16. The compound of claim 2 having the structural formula:

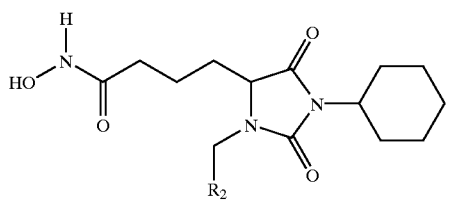

or pharmaceutically acceptable salts thereof, wherein $R_2$ is as defined in claim 2.

17. The compound of claim 16 selected from the group consisting of 4-(3-Benzyl-1-cyclohexyl-2,5-dioxo-imidazolidin-4-yl)-N-hydroxy-butyramide, 4-[1-Cyclohexyl-3-(2-hydroxy-benzyl)-2,5-dioxo-imidazolidin-4-yl]-N-hydroxy-butyramide, and 4-[1-Cyclohexyl-3-(3-hydroxy-benzyl)-2,5-dioxo-imidazolidin-4-yl]-N-hydroxy-butyramide.

18. The compound of claim 1 wherein X is S or pharmaceutically acceptable salts thereof.

19. The compound of claim 18 having the structural formula:

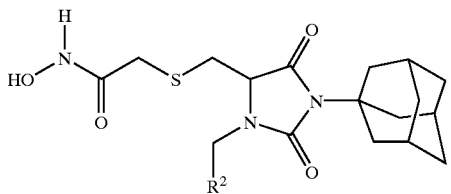

or pharmaceutically acceptable salts thereof, wherein $R_2$ is as defined in claim 1.

20. The compound of claim 1 wherein X is $NR_{19}$ or pharmaceutically acceptable salts thereof.

21. The compound of claim 20 having the structural formula:

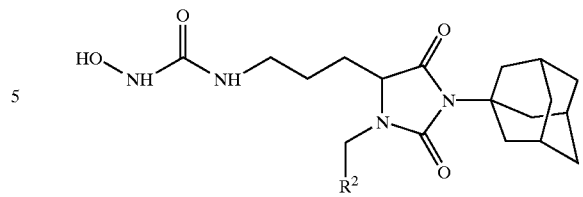

or pharmaceutically acceptable salts thereof, wherein $R_2$ is as defined in claim 1.

22. The compound of claim 1 wherein X is O or pharmaceutically acceptable salts thereof.

23. The compound of claim 1 having the structural formula:

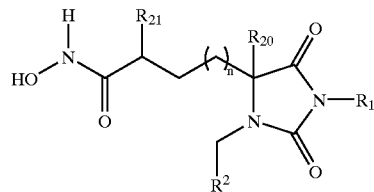

or pharmaceutically acceptable salts thereof, wherein $R_1$, $R_2$, $R_{20}$, $R_{21}$ and n are as defined in claim 1.

24. A pharmaceutical composition comprising the compound of claim 1 and a pharmaceutically acceptable carrier, diluent or excipient.

25. A method of using a compound of claim 1 to inhibit production or maturation of collagen, said method comprising the step of administering to a sample wherein collagen is being produced an effective amount of the compound or a pharmaceutical composition thereof.

26. A method of treating a fibrotic disorder selected from the group consisting of hepatic cirrhosis and arthritis, said method comprising the step of administering to a subject in need thereof an effective amount of a compound according to claim 1.

27. The method of claim 25, wherein the sample comprises a subject diagnosed with a fibrotic disorder.

28. A method of using a compound of claim 1 to inhibit C-proteinase activity, the method comprising the step of administering an effective amount of the compound to a sample containing C-proteinase or an active fragment thereof, thereby inhibiting C-proteinase activity.

* * * * *